US007033835B1

(12) United States Patent
Turpen et al.

(10) Patent No.: US 7,033,835 B1
(45) Date of Patent: Apr. 25, 2006

(54) PRODUCTION OF PEPTIDES IN PLANTS AS VIRAL COAT PROTEIN FUSIONS

(75) Inventors: Thomas H. Turpen, Vacaville, CA (US); Stephen J. Reinl, Sacramento, CA (US); Laurence K. Grill, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 135 days.

(21) Appl. No.: 09/057,016

(22) Filed: Apr. 7, 1998

Related U.S. Application Data

(63) Continuation of application No. 08/324,003, filed on Oct. 14, 1994, now Pat. No. 5,977,438, which is a continuation-in-part of application No. 08/176,414, filed on Dec. 29, 1993, now Pat. No. 5,811,653, which is a continuation-in-part of application No. 07/977,733, filed on Dec. 30, 1992, now abandoned, application No. 09/057,016, which is a continuation-in-part of application No. 08/184,237, filed on Jan. 19, 1994, now Pat. No. 5,589,367, which is a continuation-in-part of application No. 07/997,733, filed on Dec. 30, 1992, now abandoned, which is a continuation of application No. 07/923,692, filed on Jul. 31, 1992, now Pat. No. 5,316,931, which is a continuation-in-part of application No. 07/739,143, filed on Aug. 1, 1991, now abandoned, and a continuation-in-part of application No. 07/737,899, filed on Jul. 26, 1991, now abandoned, and a continuation-in-part of application No. 07/641,617, filed on Jan. 16, 1991, now abandoned, and a continuation-in-part of application No. 07/600,244, filed on Oct. 22, 1990, now abandoned, which is a continuation of application No. 07/310,881, filed on Feb. 17, 1989, now abandoned, which is a continuation-in-part of application No. 07/160,766, filed on Feb. 26, 1988, now abandoned, and a continuation-in-part of application No. 07/160,771, filed on Feb. 26, 1988, now abandoned, said application No. 07/641,617 is a continuation of application No. 07/347,637, filed on May 5, 1989, now abandoned, said application No. 07/737,899 is a continuation-in-part of application No. 07/363,138, filed on Jun. 8, 1989, now abandoned, which is a continuation-in-part of application No. 07/219,279, filed on Jul. 15, 1988, now abandoned, said application No. 07/739,143 is a continuation-in-part of application No. 07/600,244, filed on Oct. 22, 1990, now abandoned, and a continuation-in-part of application No. 07/641,617, filed on Jan. 16, 1991, now abandoned, and a continuation-in-part of application No. 07/737,899, filed on Jul. 26, 1991, now abandoned.

(51) Int. Cl.
*C12N 15/83* (2006.01)
*C12N 15/62* (2006.01)
*C12N 15/33* (2006.01)
*C12N 7/01* (2006.01)

(52) U.S. Cl. .................. 435/468; 435/69.7; 435/235.1; 435/320.1; 536/23.72

(58) Field of Classification Search ............... 435/69.7, 435/320.1, 235.1, 468; 536/23.72
See application file for complete search history.

(56) References Cited

U.S. PATENT DOCUMENTS

| 4,885,248 A | 12/1989 | Ahlquist | 435/172.3 |
|---|---|---|---|
| 5,173,410 A | 12/1992 | Ahlquist | 435/91 |
| 5,466,788 A | 11/1995 | Ahlquist | 536/24.1 |
| 5,500,360 A | 3/1996 | Ahlquist et al. | 435/172.3 |
| 5,602,242 A | 2/1997 | Ahlquist et al. | 536/23.72 |
| 5,618,699 A * | 4/1997 | Hamamoto et al. | 435/69.7 |
| 5,627,060 A | 5/1997 | Ahlquist et al. | 435/172.3 |
| 5,633,447 A | 5/1997 | Ahlquist et al. | 800/205 |
| 5,670,353 A | 9/1997 | Ahlquist et al. | 435/172.3 |

FOREIGN PATENT DOCUMENTS

| AU | B7 195 191 | 3/1992 |
|---|---|---|
| EP | 0 067 553 | 12/1982 |
| EP | 0 174 759 | 3/1986 |
| EP | 0 194 809 | 9/1986 |
| EP | 0 278 667 | 8/1988 |
| EP | 0 425 004 | 5/1991 |
| EP | 0 573 767 | 12/1993 |
| EP | 0 672 754 A1 | 9/1995 |
| JP | 61/158443 | 7/1986 |
| JP | 63-14693 | 1/1988 |
| JP | 63/200789 | 8/1988 |
| WO | WOA89 08145 | 9/1989 |
| WO | WOA90 12107 | 10/1990 |
| WO | WOA91 13994 | 9/1991 |
| WO | WO 91/15587 | 10/1991 |
| WO | 0 479 180 | 4/1992 |
| WO | WO 92/18618 | 10/1992 |

(Continued)

OTHER PUBLICATIONS

Holt et al. Virology 181:109-117, 1991.*

(Continued)

*Primary Examiner*—David T. Fox
(74) *Attorney, Agent, or Firm*—Thomas Gallegos; John C. Robbins

(57) ABSTRACT

The present invention relates to foreign peptide sequences fused to recombinant plant viral structural proteins and a method of their production. Fusion proteins are economically synthesized in plants at high levels by biologically contained tobamoviruses. The fusion proteins of the invention have many uses. Such uses include use as antigens for inducing the production of antibodies having desired binding properties, e.g., protective antibodies, or for use as vaccine antigens for the induction of protective immunity, including immunity against parasitic infections.

2 Claims, 10 Drawing Sheets

FOREIGN PATENT DOCUMENTS

| | | |
|---|---|---|
| WO | WO 93/03161 | 2/1993 |
| WO | WO 93/20217 | 10/1993 |
| WO | WO 95/21248 | 8/1995 |
| WO | WO 9602649 A1 | 2/1996 |

OTHER PUBLICATIONS

Ahlquist et al., "Viral Vectors," *Cold Spring Harbor Laboratory, New York* 183-189 (1988).
Ahlquist and Pacha, *Physiol. Plant.* 79:163-167 (1990).
Barton et al., *Plant Physiol.* 85:1103-1109 (1987).
Bruening, G., "Comovirus group, C.M.I./A.A.B. Descriptions of plant viruses," No. 199. *Wm. Culross and Son Ltd., Coupar Angus, Perthshire, Scotland.* (1978).
Butler and Mayo, "Molecular architecture and assembly of tobacco mosaic virus particles," *The molecular biology of the positive strand RNA Viruses*, Academic Press, London: 237-257 (1987).
Cassidy and Nelson, *Phytopathology* 80:1037 (1990).
Chapman et al., *Plant Journal* 2:549 (1992).
Charoenvit et al., "Inability of malaria vaccine to induce antibodies to a protective epitope within its sequence," *Science* 251:668-671 (1991).
Charoenvit et al., "Monoclonal, but not polyclonal, antibodies protect against Plasmodium yoelii sporozoites," *J. Immunol.* 146:1020-1025 (1995).
Citovsky and Zambryski, *BioEssays* 13:373-379 (1991).
Culver et al., in press, *Virology*.
Dawson and Hilf, *Ann. Rev. Plant Physiol. Plant Mol. Biol.* 43:527-555 (1992).
Dawson et al., "cDNA cloning of the complete genome of tobacco mosaic virus and production of infectious transcripts," *Proc. Natl. Acad. Sci. USA* 83:1832-1836 (1986).
Dawson et al., "Modifications of the tobacco mosaic virus coat protein gene affecting replication, movement, and symptomatology," *Phytopathol.* 78:783-789 (1988).
Dawson et al., "A Tobacco mosaic virus-hybrid expresses and loses an added gene," *Virology* 172:285-292 (1989).
Dawson, *Adv. Virus Res.* 38:307-342 (1990).
Dawson, *Virology* 186:359-367 (1992).
Deom et al., "Plant Virus Movement Proteins," *Cell* 69:221-224 (1992).
Deom et al., *Science* 237:389-394 (1987).
Dolja et al., *Proc. Natl. Acad. Sci. USA* 89:10208 (1992).
Donson et al., "Systemic expression of a bacterial gene by a tobacco mosaic virus-based vector," *Proc. Natl. Acad. Sci. USA* 88:7204-7208 (1991).
Dunsmuir et al., "Stability of introduced genes and stability of expression," Plant Molecular Biology Manual, *Kluwer Academic Publishers, Dordrecht, The Netherlands*:C1:1-17 (1988).
Fitchen et al., "Plant virus expressing hybrid coat protein with added murine epitope elicits autoantibody response," *Vaccine* 13:1051-1057 (1995).
French et al., "Bacterial ene inserted in an engineered RNA virus: Efficient expression in monocotyledonous plant cells," *Science* 231:1394-1297 (1986).
Gibbs, A.J., "Tobamovirus group, C.M.I./A.A.B. Descriptions of plant viruses," No. 184. *Wm. Culross and Son Ltd., Coupar Angus, Perthshire, Scotland* (1977).
Goelet et al., "Nucleotide sequence of tobacco mosaic virus RNA," *Proc. Natl. Acad. Sci. USA* 79:5818-5822 (1982).

Gooding, Jr., G.V., and Hebert, T.T., "A simple technique for purification of tobacco mosaic virus in large quantities," *Phytopathology* 57:1285 (1967).
Hamamoto et al., "A new tobacco mosaic virus vector and its use for the systemic production of angiotensin-I-converting enzyme inhibitor in transgenic tobacco and tomato," *Bio/Technology* 11:930-932 (1993).
Haynes et al., "Development of a genetically-engineered, candidate polio vaccine employing the self-assembling properties of the tobacco mosaic virus coat protein," *Bio/Technology* 4:637-641 (1986).
Horsch et al., "Leaf disc transformation," Plant Molecular Biology Manual, *Kluwer Academic Publishers, Dordrecht, The Netherlands*:A5:1-9 (1988).
Jagadish et al., "High Level Production of Hybrid otybirus-like Particles Carrying Repetitive Copies of Foreign Antigens in *Escherichia Coli,*" *Bio/Technology* 11:1166-1170 (1993).
Joshi and Joshi, *FEBS Letters* 281:1-8 (1991).
Joshi et al., "BSMV genome mediated expression of a foreign gene in diot and monocot plant cells," *EMBO J.* 9:2663-2669 (1990).
Jupin et al., *Virology* 178:273-280 (1990).
Kearny et al., *Virology* 192:000-000 (in press) (1993).
Krebbers et al., "Prospects and progress in the production of foreign proteins and peptides in plants," *Plant Protein Engineering.* (P.R. Shewry and S. Gutteridge, eds.), Cambridge University Press, Cambridge, pp. 315-325 (1992).
Kumagai et al., "Rapid, high level expression of biologically active α-trichosanthin in transfected plants by a novel RNA viral vector," *Proc. Natl. Acad. Sci. USA* 90:427-430 (1993).
Larkins et al., *J. Cell. Biochem. Suppl.* 0(9 Part C):264 (1985).
Martelli, *Plant Disease* 76:436 (1992).
Mason et al., "Expression of hepatitis B surface antigen in transgenic plants," *Proc. Natl. Acad. Sci. USA* 89:11745-11749 (1992).
Ogawa et al., *Virology* 185:580-584 (1991).
Ow et al., *Science* 234:856 (1986).
Pelham, H.R.B., "Leaky UAG termination codon in tobacco mosaic virus RNA," *Nature* 272:469-471 (1978).
Porta et al., "Development of Cowpea Mosaic Virus as a High-Yielding System for the Presentation of Foreign Peptides," *Virology* 202:949-955 (1994).
Potrykus, *Ann. Rev. Plant Physiol. Plant Mol. Biol.* 42:205-225 (1991).
Raffo and Dawson, "Construction of Tobacco Mosaic Virus Subgenomic Replicons that are Replicated and Spread Systemically in Tobacco Plants," *Virology* 184:277-289 (1991).
Rowlands et al., eds., *Academic Press, London*, pp. 237-257 (1987).
Saito et al., *Virology* 176:329-336 (1990).
Shaw, "Chloramphenicol acetyltransferase from chloramphenicol-resistant bacteria," *Methods in Enzymology* 53:737-755 (1975).
Skuzeski et al., "The signal for a leaky UAG stop codon in several plant viruses includes the two downstream codons," *J. Mol. Biol.* 218:365-373 (1991).
Takamatsu et al., *J. Virol.* 65:1619-1622 (1991).
Takamatsu et al., *J. Virol.* 64:3686-3693 (1990).

Takamatsu et al., "Expression of bacterial chloramphenicol acetyltransferase gene in tobacco plants mediated by TMV-RNA," *EMBO J.* 6:307-311 (1987).

Takamatsu et al., "Production of enkephalin in tobacco protoplasts using tobacco mosaic virus RNA vector," *FEBS Lett.* 269:73-76 (1990).

Turpen and Dawson, "Transgenic Plants, Fundamentals and Applications," *Marcel Dekkar, New York*, pp. 195-217 (1992).

Turpen, "Ph.D. Dissertation," *University of California, Riverside*, pp. 72-87 (1992).

Turpen, "Ph.D. Dissertation," *University of California, Riverside*, pp. 85-105 (1992).

Turpen, "Ph.D. Dissertation," *University of California, Riverside*, pp. 106-132 (1992).

Turpen and Dawson, "Amplification, movement and expression of genes in plants by viral-based vectors," *Marcel Dekkar, New York*, pp. 195-217.

Turpen, T.H., "a Molecular Genetic Analysis of Host/Viral Interactions, Implications for the Use of Plant RNA Viruses as Gene Vectors," *Chem. Abstracts* 120(9):97427 (1992).

Turpen et al., "*Malarial Epitopes* Expressed on the Surface of Recombinant Tobacco Mosaic Virus," *Bio/Technology* 10:53-57 (1995).

Usha et al., "Expression of an animal virus antigenic site on the surface of a plantvirus particle," *Virology* 197:366-374 (1993).

Van Haute et al., *EMBO J.* 2:411-417 (1983).

Von Kammen et al., "Cowpea mosaic virus, C.M.I./A.A.B. Descriptions of plant viruses," No. 197, *Wm. Culross and Son Ltd., Coupar Angus, Perthshire, Scotland*, pp. 1-5 (1978).

Velton and Schell, *NAR* 13:6981 (1985).

Walden and Schell, *Eur. J. Biochem.* 192:563-576 (1990).

Weiss et al., "A T cell clone directed at the circumsporozoite protein which protects mice against both *Plasmodium yoelii* and *Plasmodium berghei*," *J. Immunol.* 149:2103-2109 (1992).

Yamaya et al., *Mol. Gen. Genet.* 211:520-525 (1988).

Zaitlin et al., "Tobacco mosaic virus (type strain), C.M.I./A.A.B. Descriptions of plant viruses, " No. 151, *Wm. Culross and Son Ltd., Coupar Angus, Perthshire, Scotland*, pp. 1-6 (1975).

Zaitlin and Hull, *Ann. Rev. Plant Physiol.* 38:291-315 (1987).

Zambryski et al., *EMBO J.* 2:2143-2150 (1983).

\* cited by examiner

PRODUCTION OF PEPTIDES IN PLANTS AS VIRAL COAT PROTEIN FUSIONS

CROSS-REFERENCE TO RELATED APPLICATIONS

The present application is a continuation of application Ser. No. 08/324,003, filed Oct. 14, 1994, now U.S. Pat. No. 5,977,438, which is a continuation-in-part of application Ser. No. 08/176,414, filed on Dec. 29, 1993, now U.S. Pat. No. 5,811,653, which is a continuation-in-part of abandoned application Ser. No. 07/997,733, filed Dec. 30, 1992. The present application is a continuation-in-part of application Ser. No. 08/184,237, filed Jan. 19, 1994, now U.S. Pat. No. 5,589,367, which is a continuation-in-part of application Ser. No. 07/997,733, filed Dec. 30, 1992, now abandoned, which is a continuation of application Ser. No. 07/923,692, filed Jul. 31, 1992, now U.S. Pat. No. 5,316,931, which is a continuation-in-part of applications Ser. No. 07/600,244, filed Oct. 22, 1990, now abandoned, Ser. No. 07/641,617, filed Jan. 16, 1991, now abandoned, application Ser. No. 07/737,899, filed Jul. 26, 1991, now abandoned, and application Ser. No. 07/739,143, filed Aug. 1, 1991, now abandoned. Application Ser. No. 07/600,244 is a continuation of application Ser. No. 07/310,881, filed Feb. 17, 1989, now abandoned, which is a continuation-in-part of applications Ser. No. 07/160,766 and Ser. No. 07/160,771, both filed on Feb. 26, 1988 and now abandoned. Application Ser. No. 07/641,617 is a continuation of application Ser. No. 07/347,637, filed May 5, 1989, now abandoned. Application Ser. No. 07/737,899 is a continuation of application Ser. No. 07/363,138, filed Jun. 8, 1989, now abandoned, which is a continuation-in-part of Application No. 07/219,279, filed Jul. 15, 1988, now abandoned. Application Ser. No. 07/739,143 is a continuation-in-part of Applications No. 07/600,244, filed Oct. 22, 1990, now abandoned, No. 07/641,617, filed Jan. 16, 1991, now abandoned, and No. 07/737,899, filed Jul. 26, 1991, now abandoned.

FIELD OF THE INVENTION

The present invention relates to the field of genetically engineered peptide production in plants, more specifically, the invention relates to the use of tobamovirus vectors to express fusion proteins.

BACKGROUND OF THE INVENTION

Peptides are a diverse class of molecules having a variety of important chemical and biological properties. Some examples include; hormones, cytokines, immunoregulators, peptide-based enzyme inhibitors, vaccine antigens, adhesions, receptor binding domains, enzyme inhibitors and the like. The cost of chemical synthesis limits the potential applications of synthetic peptides for many useful purposes such as large scale therapeutic drug or vaccine synthesis. There is a need for inexpensive and rapid synthesis of milligram and larger quantities of naturally-occurring polypeptides. Towards this goal many animal and bacterial viruses have been successfully used as peptide carriers.

The safe and inexpensive culture of plants provides an improved alternative host for the cost-effective production of such peptides. During the last decade, considerable progress has been made in expressing foreign genes in plants. Foreign proteins are now routinely produced in many plant species for modification of the plant or for production of proteins for use after extraction. Animal proteins have been effectively produced in plants (reviewed in Krebbers et al., 1992).

Vectors for the genetic manipulation of plants have been derived from several naturally occurring plant viruses, including TMV (tobacco mosaic virus). TMV is the type member of the tobamovirus group. TMV has straight tubular virions of approximately 300×18 nm with a 4 nm-diameter hollow canal, consisting of approximately 2000 units of a single capsid protein wound helically around a single RNA molecule. Virion particles are 95% protein and 5% RNA by weight. The genome of TMV is composed of a single-stranded RNA of 6395 nucleotides containing five large ORFs. Expression of each gene is regulated independently. The virion RNA serves as the messenger RNA (mRNA) for the 5' genes, encoding the 126 kDa replicase subunit and the overlapping 183 kDa replicase subunit that is produced by read through of an amber stop codon approximately 5% of the time. Expression of the internal genes is controlled by different promoters on the minus-sense RNA that direct synthesis of 3'-coterminal subgenomic mRNAs which are produced during replication (FIG. 1). A detailed description of tobamovirus gene expression and life cycle can be found, among other places, in Dawson and Lehto, *Advances in Virus Research* 38:307–342 (1991). It is of interest to provide new and improved vectors for the genetic manipulation of plants.

For production of specific proteins, transient expression of foreign genes in plants using virus-based vectors has several advantages. Products of plant viruses are among the highest produced proteins in plants. Often a viral gene product is the major protein produced in plant cells during virus replication. Many viruses are able to quickly move from an initial infection site to almost all cells of the plant. Because of these reasons, plant viruses have been developed into efficient transient expression vectors for foreign genes in plants. Viruses of multicellular plants are relatively small, probably due to the size limitation in the pathways that allow viruses to move to adjacent cells in the systemic infection of entire plants. Most plant viruses have single-stranded RNA genomes of less than 10 kb. Genetically altered plant viruses provide one efficient means of transfecting plants with genes coding for peptide carrier fusions.

SUMMARY OF THE INVENTION

The present invention provides recombinant plant viruses that express fusion proteins that are formed by fusions between a plant viral coat protein and protein of interest. By infecting plant cells with the recombinant plant viruses of the invention, relatively large quantities of the protein of interest may be produced in the form of a fusion protein. The fusion protein encoded by the recombinant plant virus may have any of a variety of forms. The protein of interest may be fused to the amino terminus of the viral coat protein or the protein of interest may be fused to the carboxyl terminus of the viral coat protein. In other embodiments of the invention, the protein of interest may be fused internally to a coat protein. The viral coat fusion protein may have one or more properties of the protein of interest. The recombinant coat fusion protein may be used as an antigen for antibody development or to induce a protective immune response.

Another aspect of the invention is to provide polynucleotides encoding the genomes of the subject recombinant plant viruses. Another aspect of the invention is to provide the coat fusion proteins encoded by the subject recombinant plant viruses. Yet another embodiment of the invention is to provide plant cells that have been infected by the recombinant plant viruses of the invention.

DESCRIPTION OF THE SPECIFIC EMBODIMENTS

Figure 1:
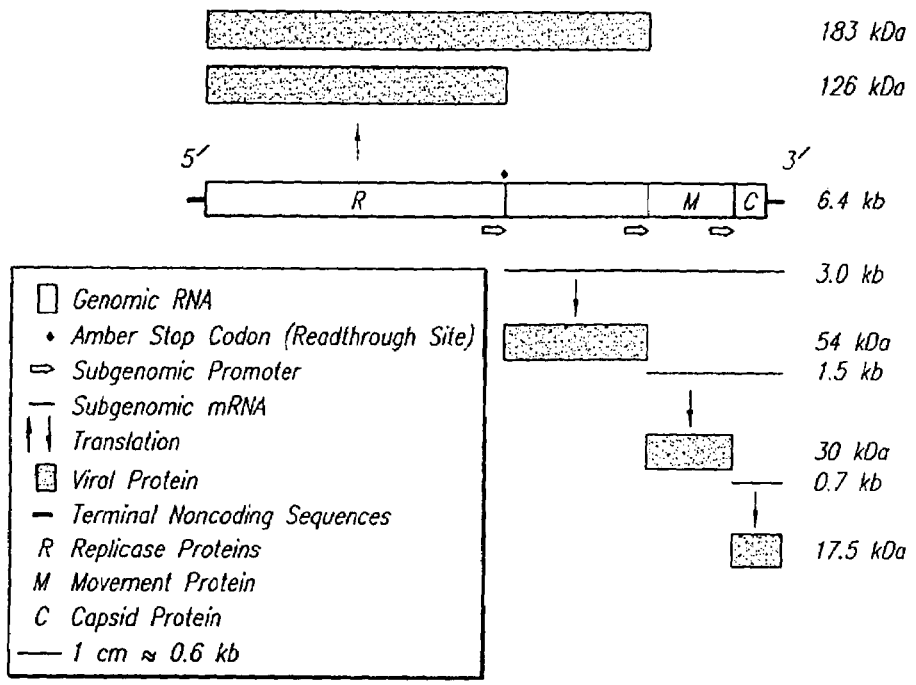
FIG. 1. Tobamovirus Gene Expression
The gene expression of tobamoviruses is diagrammed.

Definitions and Abbreviations
TMV: Tobacco mosaic tobamovirus
TMVCP: Tobacco mosaic tobamovirus coat protein
Viral Particles: High molecular weight aggregates of viral structural proteins with or without genomic nucleic acids
Virion: An infectious viral particle.

The Invention

The subject invention provides novel recombinant plant viruses that code for the expression of fusion proteins that consist of a fusion between a plant viral coat protein and a protein of interest. The recombinant plant viruses of the invention provide for systemic expression of the fusion protein, by systemically infecting cells in a plant. Thus by employing the recombinant plant viruses of the invention, large quantities of a protein of interest may be produced.

The fusion proteins of the invention comprise two portions: (i) a plant viral coat protein and (ii) a protein of interest. The plant viral coat protein portion may be derived from the same plant viral coat protein that serves a coat protein for the virus from which the genome of the expression vector is primarily derived, i.e., the coat protein is native with respect to the recombinant viral genome. Alternatively, the coat protein portion of the fusion protein may be heterologous, i.e., non-native, with respect to the recombinant viral genome. In a preferred embodiment of the invention, the 17.5 KDa coat protein of tobacco mosaic virus is used in conjunction with a tobacco mosaic virus derived vector. The protein of interest portion of the fusion protein for expression may consist of a peptide of virtually any amino acid sequence, provided that the protein of interest does not significantly interfere with (1) the ability to bind to a receptor molecule, including antibodies and T cell receptor (2) the ability to bind to the active site of an enzyme (3) the ability to induce an immune response, (4) hormonal activity, (5) immunoregulatory activity, and (6) metal chelating activity. The protein of interest portion of the subject fusion proteins may also possess additional chemical or biological properties that have not been enumerated. Protein of interest portions of the subject fusion proteins having the desired properties may be obtained by employing all or part of the amino acid residue sequence of a protein known to have the desired properties. For example, the amino acid sequence of hepatitis B surface antigen may be used as a protein of interest portion of a fusion protein invention so as to produce a fusion protein that has antigenic properties similar to hepatitis B surface antigen. Detailed structural and functional information about many proteins of interest are well known, this information may be used by the person of ordinary skill in the art so as to provide for coat fusion proteins having the desired properties of the protein of interest. The protein of interest portion of the subject fusion proteins may vary in size from one amino acid residue to over several hundred amino acid residues, preferably the sequence of interest portion of the subject fusion protein is less than 100 amino acid residues in size, more preferably, the sequence of interest portion is less than 50 amino acid residues in length. It will be appreciated by those of ordinary skill in the art that, in some embodiments of the invention, the protein of interest portion may need to be longer than 100 amino acid residues in order to maintain the desired properties. Preferably, the size of the protein of interest portion of the fusion proteins of the invention is minimized (but retains the desired biological/chemical properties), when possible.

While the protein of interest portion of fusion proteins of the invention may be derived from any of the variety of proteins, proteins for use as antigens are particularly preferred. For example, the fusion protein, or a portion thereof, may be injected into a mammal, along with suitable adjutants, so as to produce an immune response directed against the protein of interest portion of the fusion protein. The immune response against the protein of interest portion of the fusion protein has numerous uses, such uses include, protection against infection, and the generation of antibodies useful in immunoassays.

The location (or locations) in the fusion protein of the invention where the viral coat protein portion is joined to the protein of interest is referred to herein as the fusion joint. A given fusion protein may have one or two fusion joints. The fusion joint may be located at the carboxyl terminus of the coat protein portion of the fusion protein (joined at the amino terminus of the protein of interest portion). The fusion joint may be located at the amino terminus of the coat protein portion of the fusion protein (joined to the carboxyl terminus of the protein of interest). In other embodiments of the invention, the fusion protein may have two fusion joints. In those fusion proteins having two fusion joints, the protein of interest is located internal with respect to the carboxyl and amino terminal amino acid residues of the coat protein portion of the fusion protein, i.e., an internal fusion protein. Internal fusion proteins may comprise an entire plant virus coat protein amino acid residue sequence (or a portion thereof) that is "interrupted" by a protein of interest, i.e., the amino terminal segment of the coat protein portion is joined at a fusion joint to the amino terminal amino acid residue of the protein of interest and the carboxyl terminal segment of the coat protein is joined at a fusion joint to the amino terminal acid residue of the protein of interest.

When the coat fusion protein for expression is an internal fusion protein, the fusion joints may be located at a variety of sites within a coat protein. Suitable sites for the fusion joints may be determined either through routine systematic variation of the fusion joint locations so as to obtain an internal fusion protein with the desired properties. Suitable sites for the fusion jointly may also be determined by analysis of the three dimensional structure of the coat protein so as to determine sites for "insertion" of the protein of interest that do not significantly interfere with the structural and biological functions of the coat protein portion of the fusion protein. Detailed three dimensional structures of plant viral coat proteins and their orientation in the virus have been determined and are publicly available to a person of ordinary skill in the art. For example, a resolution model of the coat protein of Cucumber Green Mottle Mosaic Virus (a coat protein bearing strong structural similarities to other tobamovirus coat proteins) and the virus can be found in Wang and Stubbs *J. Mol. Biol.* 239:371–384 (1994). Detailed structural information on the virus and coat protein of Tobacco Mosaic Virus can be found, among other places in Namba et al, *J. Mol. Biol.* 208:307–325 (1989) and Pattanayek and Stubbs *J. Mol. Biol.* 228:516–528 (1992).

Knowledge of the three dimensional structure of a plant virus particle and the assembly process of the virus particle permits the person of ordinary skill in the art to design various coat protein fusions of the invention, including insertions, and partial substitutions. For example, if the protein of interest is of a hydrophilic nature, it may be appropriate to fuse the peptide to the TMVCP region known to be oriented as a surface loop region. Likewise, alpha helical segments that maintain subunit contacts might be substituted for appropriate regions of the TMVCP helices or nucleic acid binding domains expressed in the region of the TMVCP oriented towards the genome.

Polynucleotide sequences encoding the subject fusion proteins may comprise a "leaky" stop codon at a fusion joint. The stop codon may be present as the codon immediately adjacent to the fusion joint, or may be located close (e.g., within 9 bases) to the fusion joint. A leaky stop codon may be included in polynucleotides encoding the subject coat fusion proteins so as to maintain a desired ratio of fusion protein to wild type coat protein. A "leaky" stop codon does not always result in translational termination and is periodically translated. The frequency of initiation or termination at a given start/stop codon is context dependent. The ribosome scans from the 5'-end of a messenger RNA for the first ATG codon. If it is in a non-optimal sequence context, the ribosome will pass, some fraction of the time, to the next available start codon and initiate translation downstream of the first. Similarly, the first termination codon encountered during translation will not function 100% of the time if it is in a particular sequence context. Consequently, many naturally occurring proteins are known to exist as a population having heterogeneous N and/or C terminal extensions. Thus by including a leaky stop codon at a fusion joint coding region in a recombinant viral vector encoding a coat fusion protein, the vector may be used to produce both a fusion protein and a second smaller protein, e.g., the viral coat protein. A leaky stop codon may be used at, or proximal to, the fusion joints of fusion proteins in which the protein of interest portion is joined to the carboxyl terminus of the coat protein region, whereby a single recombinant viral vector may produce both coat fusion proteins and coat proteins. Additionally, a leaky start codon may be used at or proximal to the fusion joints of fusion proteins in which the protein of interest portion is joined to the amino terminus of the coat protein region, whereby a similar result is achieved. In the case of TMVCP, extensions at the N and C terminus are at the surface of viral particles and can be expected to project away from the helical axis. An example of a leaky stop sequence occurs at the junction of the 126/183 kDa reading frames of TMV and was described over 15 years ago (Pelham, H. R. B., 1978). Skuzeski et al. (1991) defined necessary 3' context requirements of this region to confer leakiness of termination on a heterologous protein marker gene (β-glucuronidase) as CAR-YYA (C=cytidine, A=adenine, Y=pyrimidine).

In another embodiment of the invention, the fusion joints on the subject coat fusion proteins are designed so as to comprise an amino acid sequence that is a substrate for protease. By providing a coat fusion protein having such a fusion joint, the protein of interest may be conveniently derived from the coat protein fusion by using a suitable proteolytic enzyme. The proteolytic enzyme may contact the fusion protein either in vitro or in vivo.

The expression of the subject coat fusion proteins may be driven by any of a variety of promoters functional in the genome of the recombinant plant viral vector. In a preferred embodiment of the invention, the subject fusion proteins are expressed from plant viral subgenomic promoters using vectors as described in U.S. Pat. No. 5,316,931.

Recombinant DNA technologies have allowed the life cycle of numerous plant RNA viruses to be extended artificially through a DNA phase that facilitates manipulation of the viral genome. These techniques may be applied by the person ordinary skill in the art in order make and use recombinant plant viruses of the invention. The entire cDNA of the TMV genome was cloned and functionally joined to a bacterial promoter in an *E. coli* plasmid (Dawson et al., 1986). Infectious recombinant plant viral RNA transcripts may also be produced using other well known techniques, for example, with the commercially available RNA polymerases from T7, T3 or SP6. Precise replicas of the virion RNA can be produced in vitro with RNA polymerase and dinucleotide cap, m7 GpppG. This not only allows manipulation of the viral genome for reverse genetics, but it also allows manipulation of the virus into a vector to express foreign genes. A method of producing plant RNA virus vectors based on manipulating RNA fragments with RNA ligase has proved to be impractical and is not widely used (Pelcher, L. E., 1982). Detailed information on how to make and use recombinant RNA plant viruses can be found, among other places in U.S. Pat. No. 5,316,931 (Donson et al.), which is herein incorporated by reference. The invention provides for polynucleotide encoding recombinant RNA plant vectors for the expression of the subject fusion proteins. The invention also provides for polynucleotides comprising a portion or portions of the subject vectors. The vectors described in U.S. Pat. No. 5,316,931 are particularly preferred for expressing the fusion proteins of the invention.

In addition to providing the described viral coat fusion proteins, the invention also provides for virus particles that comprise the subject fusion proteins. The coat of the virus particles of the invention may consist entirely of coat fusion protein. In another embodiment of the virus particles of the invention, the virus particle coat may consist of a mixture of coat fusion proteins and non-fusion coat protein, wherein the ratio of the two proteins may be varied. As tobamovirus coat proteins may self-assemble into virus particles, the virus particles of the invention may be assembled either in vivo or in vitro. The virus particles may also be conveniently disassembled using well known techniques so as to simplify the purification of the subject fusion proteins, or portions thereof.

The invention also provides for recombinant plant ells comprising the subject coat fusion proteins and/or virus articles comprising the subject coat fusion proteins. These lant cells may be produced either by infecting plant cells (either in culture or in whole plants) with infectious virus articles of the invention or with polynucleotides encoding the genomes of the infectious virus particle of the invention. The recombinant plant cells of the invention have many uses. Such uses include serving as a source for the fusion coat proteins of the invention.

The protein of interest portion of the subject fusion proteins may comprise many different amino acid residue sequences, and accordingly may have different possible biological/chemical properties however, in a preferred embodiment of the invention the protein of interest portion of the fusion protein is useful as a vaccine antigen. The surface of TMV particles and other tobamoviruses contain continuous epitopes of high antigenicity and segmental mobility thereby making TMV particles especially useful in producing a desired immune response. These properties make the virus particles of the invention especially useful as carriers in the presentation of foreign epitopes to mammalian immune systems.

While the recombinant RNA viruses of the invention may be used to produce numerous coat fusion proteins for use as vaccine antigens or vaccine antigen precursors, it is of particular interest to provide vaccines against malaria. Human malaria is caused by the protozoan species *Plasmodium falciparum*, *P. vivax*, *P. ovale* and *P. malariae* and is transmitted in the sporozoite form by *Anopheles* mosquitos. Control of this disease will likely require safe and stable vaccines. Several peptide epitopes expressed during various stages of the parasite life cycle are thought to contribute to the induction of protective immunity in partially resistant individuals living in endemic areas and in individuals experimentally immunized with irradiated sporozoites.

When the fusion proteins of the invention, portions thereof, or viral particles comprising the fusion proteins are used in vivo, the proteins are typically administered in a composition comprising a pharmaceutical carrier. A pharmaceutical carrier can be any compatible, non-toxic substance suitable for delivery of the desired compounds to the body. Sterile water, alcohol, fats, waxes and inert solids may be included in the carrier. Pharmaceutically accepted adjuvants (buffering agents, dispersing agent) may also be incorporated into the pharmaceutical composition. Additionally, when the subject fusion proteins, or portion thereof, are to be used for the generation of an immune response, protective or otherwise, formulation for administration may comprise one or immunological adjuvants in order to stimulate a desired immune response.

When the fusion proteins of the invention, or portions thereof, are used in vivo, they may be administered to a subject, human or animal, in a variety of ways. The pharmaceutical compositions may be administered orally or parenterally, i.e., subcutaneously, intramuscularly or intravenously. Thus, this invention provides compositions for parenteral administration which comprise a solution of the fusion protein (or derivative thereof) or a cocktail thereof dissolved in an acceptable carrier, preferably an aqueous carrier. A variety of aqueous carriers can be used, e.g., water, buffered water, 0.4% saline, 0.3% glycerine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of fusion protein (or portion thereof) in these formulations can vary widely depending on the specific amino acid sequence of the subject proteins and the desired biological activity, e.g., from less than about 0.5%, usually at or at least about 1% to as much as 15 or 20% by weight and will be selected primarily based on fluid volumes, viscosities, etc., in accordance with the particular mode of administration selected.

Actual methods for preparing parenterally administrable compositions and adjustments necessary for administration to subjects will be known or apparent to those skilled in the art and are described in more detail in, for example, *Remington's Pharmaceutical Science*, current edition, Mack Publishing Company, Easton, Pa., which is incorporated herein by reference.

The invention having been described above, may be better understood by reference to the following examples. The examples are offered by way of illustration and are not intended to be interpreted as limitations on the scope of the invention.

EXAMPLES

Biological Deposits

Figure 2:
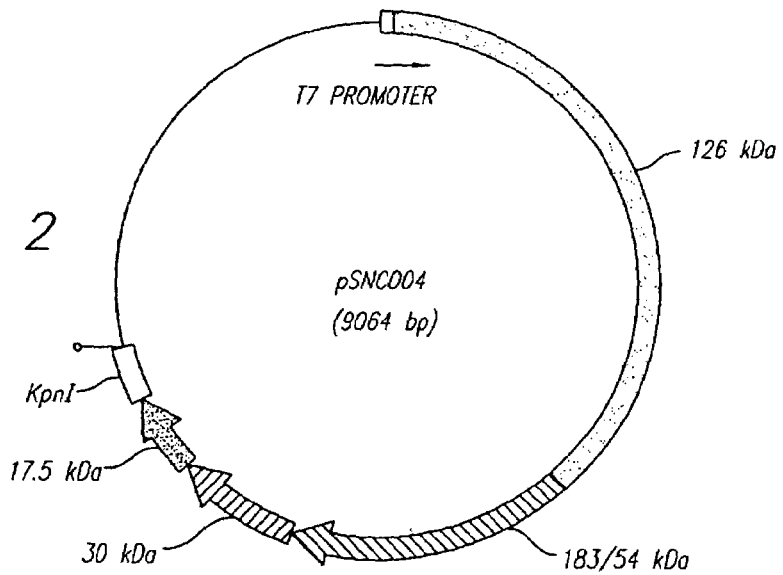
FIG. 2. Plasmid Map of the TMV Transcription Vector pSNC004
The infectious RNA genome of the U1 strain of TMV is synthesized by T7 RNA polymerase in vitro from pSNC004 linearized with KpnI.
Figures 1, 3A:
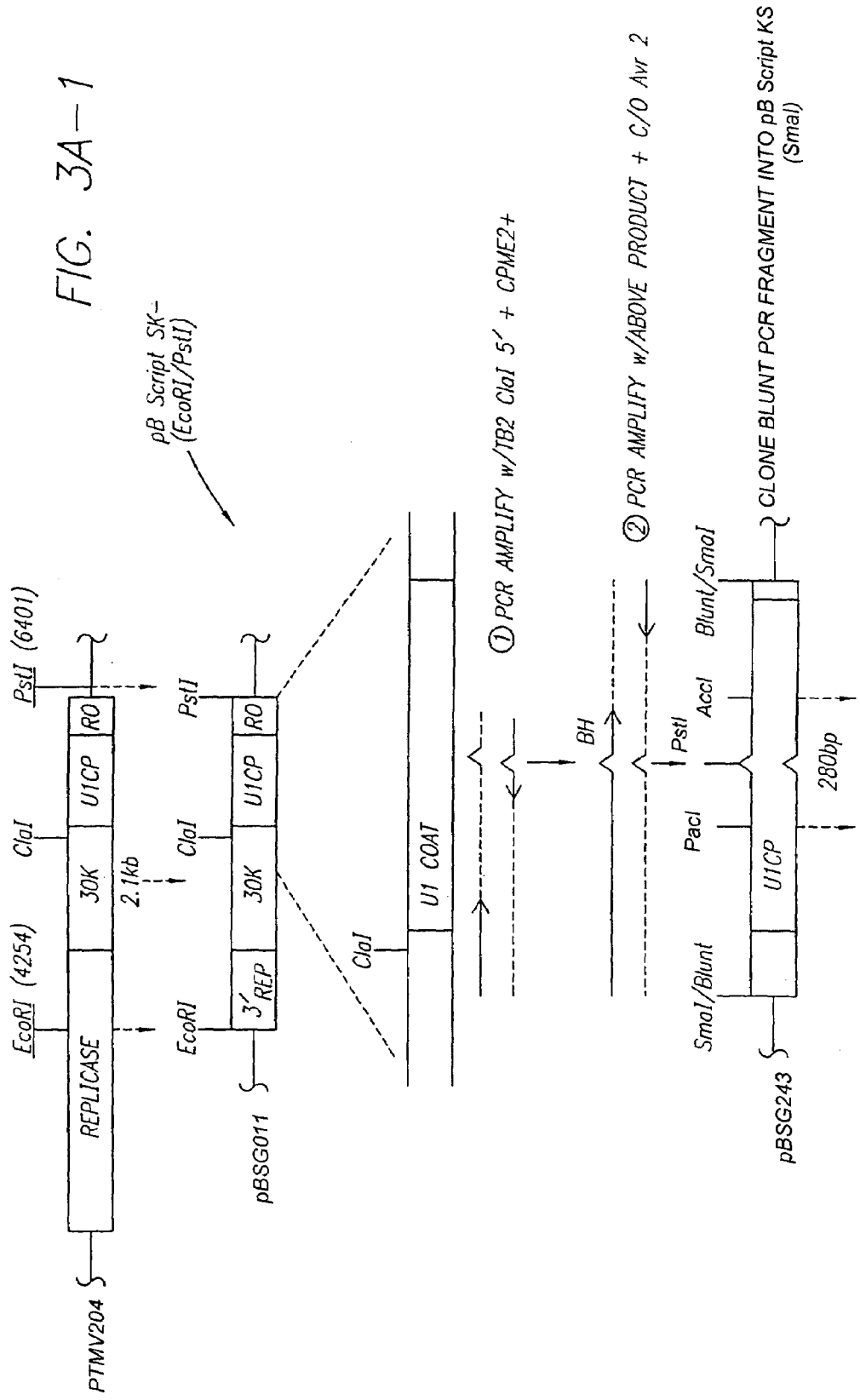
FIG. 3A–3C. Diagram of Plasmid Constructions
Each step in the construction of plasmid DNAs encoding various viral epitope fusion vectors discussed in the examples is diagrammed.
Figures 2, 3A:
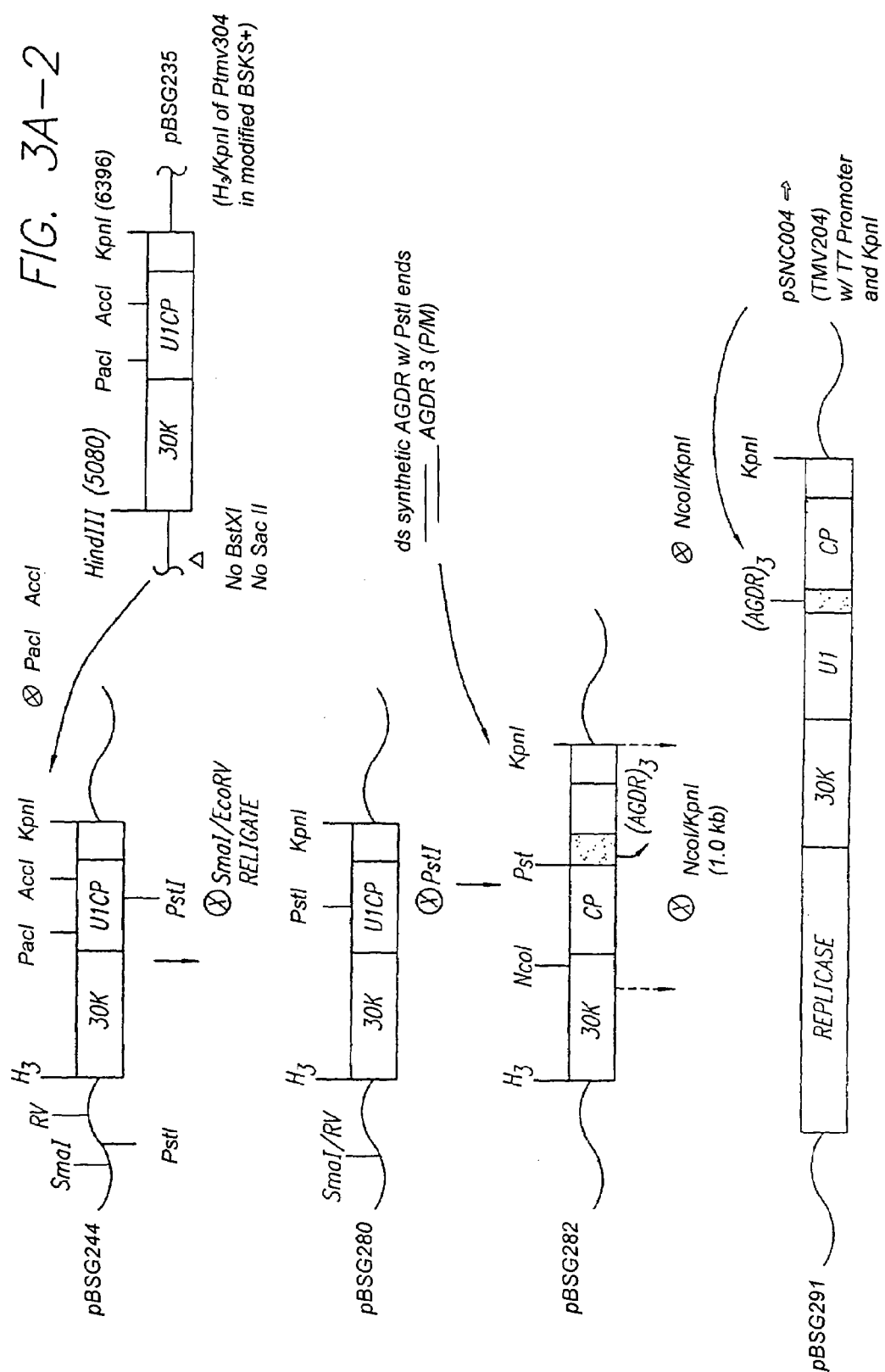
Figures 1, 3B:
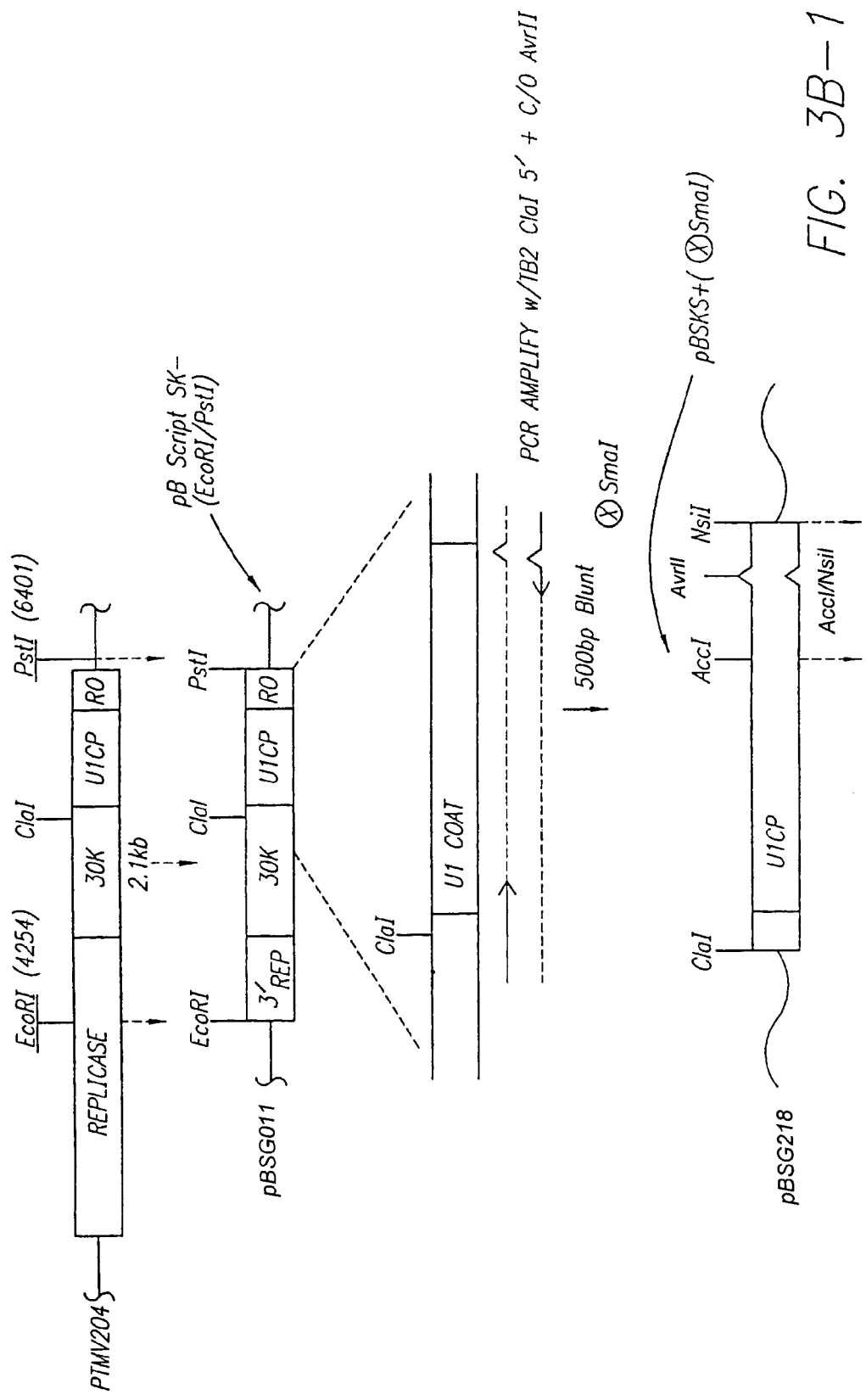
Figures 2, 3B:
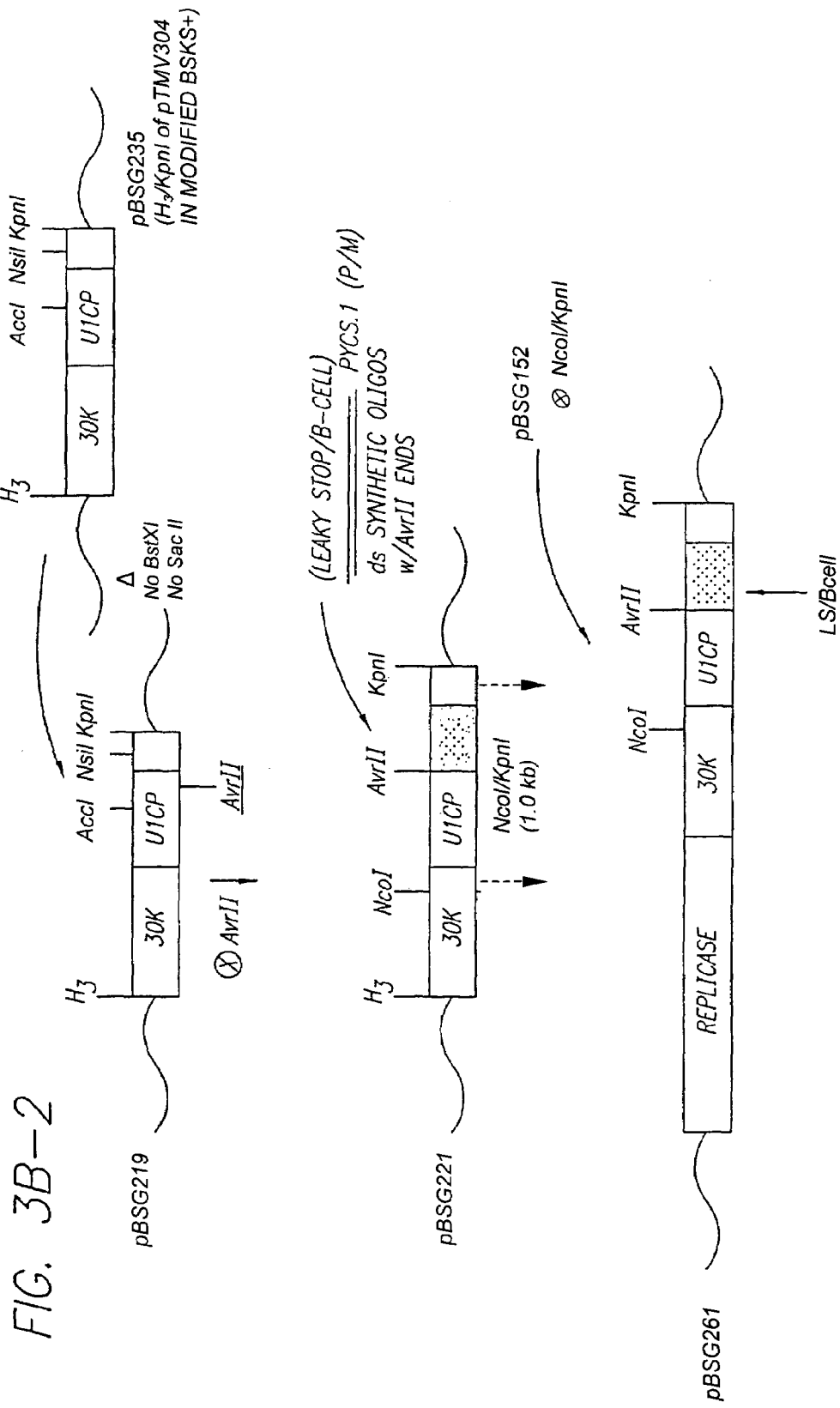
Figures 1, 3C:
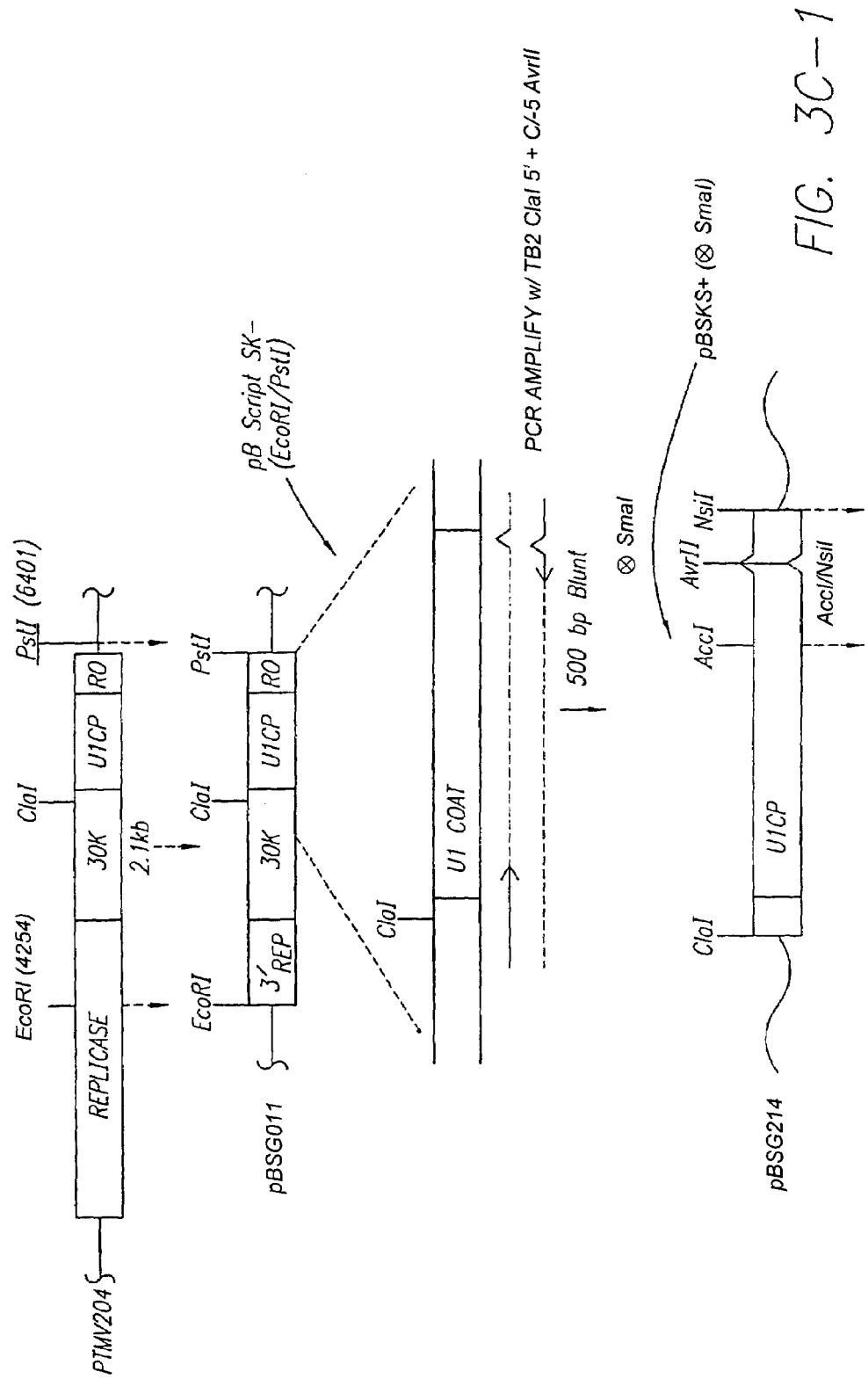
Figures 2, 3C:
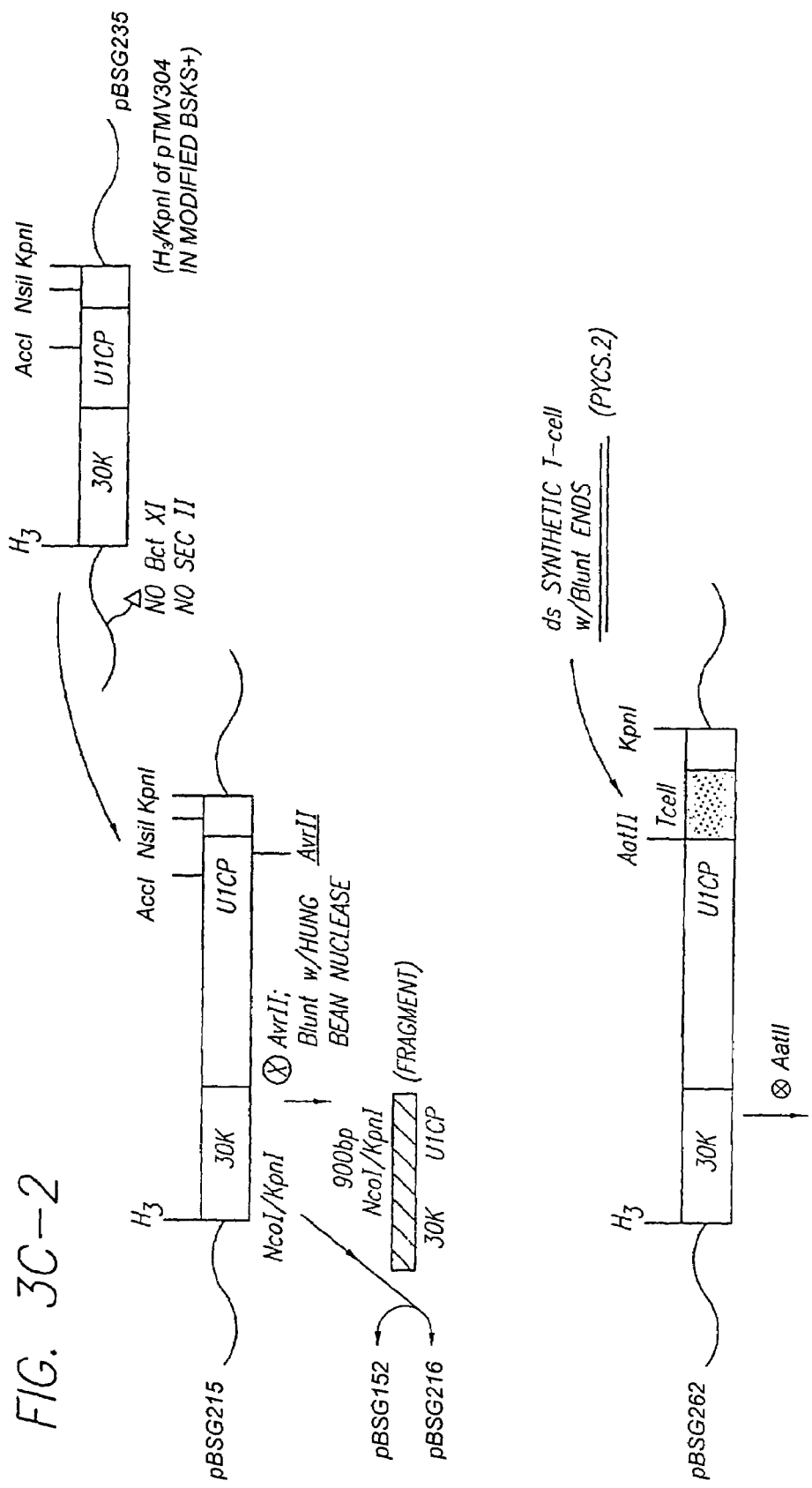
Figures 3, 3C:
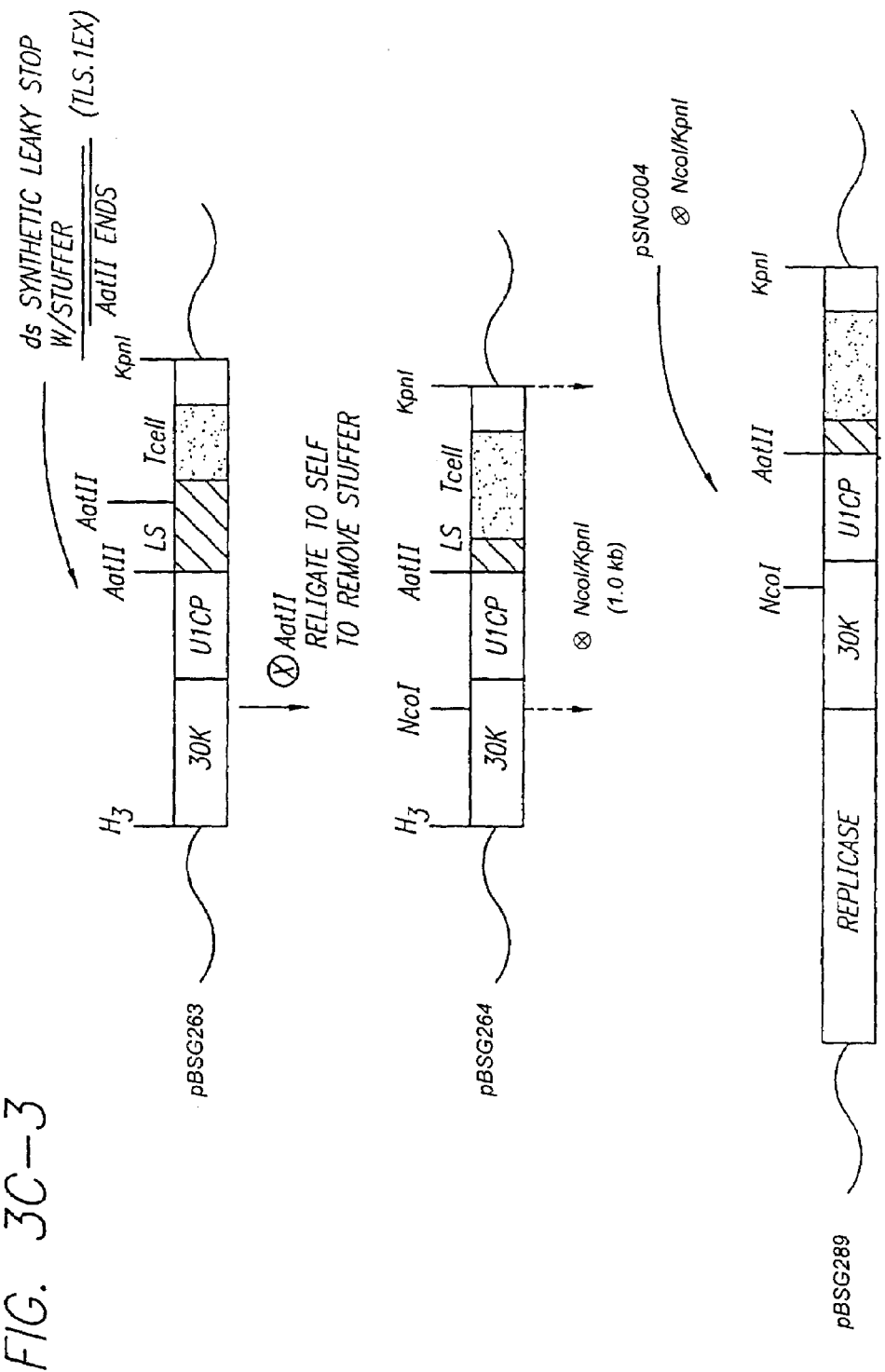

The following present examples are based on a full length insert of wild type TMV (U1 strain) cloned in the vector pUC18 with a T7 promoter sequence at the 5'-end and a KpnI site at the 3'-end (pSNC0004, FIG. 2) or a similar plasmid pTMV304. Using the polymerase chain reaction (PCR) technique and primers WD29 (SEQ ID NO: 1) and D1094 (SEQ ID NO: 2) a 277 XmaI/HindIII amplification product was inserted with the 6140 bp XmaI/KpnI fragment from pTMV304 between the KpnI and HindIII sites of the common cloning vector pUC18 to create pSNC004. The plasmid pTMV304 is available from the American Type Culture Collection, Rockville, Md. (ATCC deposit 45138). The genome of the wild type TMV strain can be synthesized from pTMV304 using the SP6 polymerase, or from pSNC004 using the T7 polymerase. The wild type TMV strain can also be obtained from the American Type Culture Collection, Rockville, Md. (ATCC deposit No. PV135). The plasmid pBGC152, Kumagai, M., et al., (1993), is a derivative of pTMV304 and is used only as a cloning intermediate in the examples described below. The construction of each plasmid vector described in the examples below is diagrammed in FIG. 3.

Example 1

Propagation and purification of the U1 strain of TMV

The TMVCP fusion vectors described in the following examples are based on the U1 or wild type TMV strain and are therefore compared to the parental virus as a control. *Nicotiana tabacum* cv Xanthi (hereafter referred to as tobacco) was grown 4–6 weeks after germination, and two 4–8 cm expanded leaves were inoculated with a solution of 50 µg/ml TMV U1 by pipetting 100 µl onto carborundum dusted leaves and lightly abrading the surface with a gloved hand. Six tobacco plants were grown for 27 days post inoculation accumulating 177 g fresh weight of harvested leaf biomass not including the two lower inoculated leaves. Purified TMV U1 Sample ID No. TMV204.B4 was recovered (745 mg) at a yield of 4.2 mg of virion per gram of fresh weight by two cycles of differential centrifugation and precipitation with PEG according to the method of Gooding et al. (1967). Tobacco plants infected with TMV U1 accumulated greater than 230 micromoles of coat protein per kilogram of leaf tissue.

Example 2

Production of a malarial B-cell epitope genetically fused to the surface loop region of the TMVCP The monoclonal antibody NVS3 was made by immunizing a mouse with irradiated *P. vivax* sporozoites. NVS3 mAb passively transferred to monkeys provided protective immunity to sporozoite infection with this human parasite. Using the technique of epitope-scanning with synthetic peptides, the exact amino acid sequence present on the *P. vivax* sporozoite surface and recognized by NVS3 was defined as AGDR (Seq ID No. P1). The epitope AGDR is contained within a repeating unit of the circumsporozoite (CS) protein (Charoenvit et al., 1991a), the major immunodominant protein coating the sporozoite. Construction of a genetically modified tobamovirus designed to carry this malarial B-cell epitope fused to the surface of virus particles is set forth herein.

Construction of plasmid pBGC291. The 2.1 kb EcoRI-PstI fragment from pTMV204 described in Dawson, W., et al. (1986) was cloned into pBstSK+ (Stratagene Cloning Systems) to form pBGC11. A 0.27 kb fragment of pBGC11 was PCR amplified using the 5' primer TB2ClaI5' (SEQ ID NO: 3) and the 3' primer CP.ME2+ (SEQ ID NO: 4). The 0.27 kb amplified product was used as the 51 primer and C/0AvrII (SEQ ID NO: 5) was the 3' primer for PCR amplification. The amplified product was cloned into the SmaI site of pBstKS+ (Stratagene Cloning Systems) to form pBGC243.

To eliminate the BstXI and SacII sites from the polylinker, pBGC234 was formed by digesting pBstKS+(Stratagene Cloning Systems) with BstXI followed by treatment with T4 DNA Polymerase and self-ligation. The 1.3 kb HindIII-KpnI fragment of pBGC304 was cloned into pBGC234 to form pBGC235. pBGC304 is also named pTMV304 (ATCC deposit 45138).

The 0.3 kb PacI-AccI fragment of pBGC243 was cloned into pBGC235 to form pBGC244. The 0.02 kb polylinker fragment of pBGC243 (SmaI-EcoRV) was removed to form pBGC280. A 0.02 kb synthetic PstI fragment encoding the *P. vivax* AGDR repeat was formed by annealing AGDR3p (SEQ ID NO: 6) with AGDR3m (SEQ ID NO: 7) and the resulting double stranded fragment was cloned into pBGC280 to form pBGC282. The 1.0 kb NcoI-KpnI fragment of pBGC282 was cloned into pSNC004 to form pBGC291.

The coat protein sequence of the virus TMV291 produced by transcription of plasmid pBGC291 in vitro is listed in (SEQ ID NO: 16) The epitope (AGDR)3 is calculated to be approximately 6.2% of the weight of the virion.

Propagation and purification of the epitope expression vector. Infectious transcripts were synthesized from KpnI-linearized pBGC291 using T7 RNA polymerase and cap (7mGpppG) according to the manufacturer (New England Biolabs).

An increased quantity of recombinant virus was obtained by passaging and purifying Sample ID No. TMV291.1B1 as described in example 1. Twenty tobacco plants were grown for 29 days post inoculation, accumulating 1060 g fresh weight of harvested leaf biomass not including the two lower inoculated leaves. Purified Sample ID TMV291.1B2 was recovered (474 mg) at a yield of 0.4 mg virion per gram of fresh weight. Therefore, 25 µg of 12-mer peptide was obtained per gram of fresh weight extracted. Tobacco plants infected with TMV291 accumulated greater than 21 micromoles of peptide per kilogram of leaf tissue.

Figure 4:
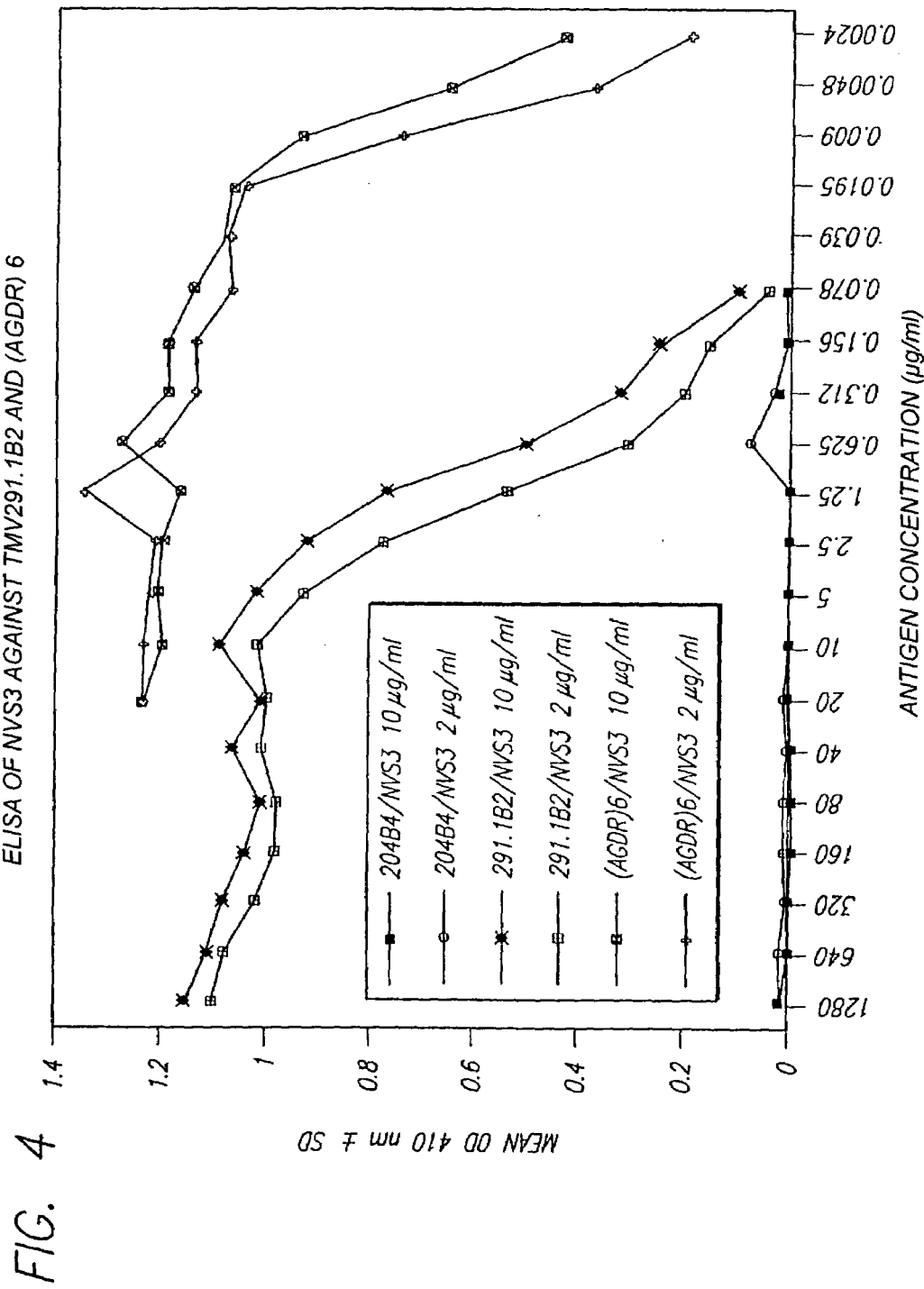
FIG. 4. Monoclonal Antibody (NVS3) Binding to TMV291
The reactivity of NVS3 to the malaria epitope present in TMV291 is measured in a standard ELISA.

Product analysis. The conformation of the epitope AGDR contained in the virus TMV291 is specifically recognized by the monoclonal antibody NVS3 in ELISA assays (FIG. 4). By Western blot analysis, NVS3 cross-reacted only with the TMV291 cp fusion at 18.6 kD and did not cross-react with the wild type or cp fusion present in TMV261. The genomic sequence of the epitope coding region was confirmed by directly sequencing viral RNA extracted from Sample ID No. TMV291.1B2.

Example 3

Production of a malarial B-cell epitope genetically fused to the C terminus of the TMVCP Significant progress has been made in designing effective subunit vaccines using rodent models of malarial disease caused by nonhuman pathogens such as *P. yoelii* or *P. berghei*. The monoclonal antibody NYS1 recognizes the repeating epitope QGPGAP (SEQ ID NO: 18), present on the CS protein of *P. yoelii*, and provides a very high level of immunity to sporozoite challenge when passively transferred to mice (Charoenvit, Y., et al. 1991b). Construction of a genetically modified tobamovirus designed to carry this malarial B-cell epitope fused to the surface of virus particles is set forth herein.

Construction of plasmid pBGC261. A 0.5 kb fragment of pBGC11, was PCR amplified using the 5' primer TB2ClaI5' (SEQ ID NO: 3) and the 3' primer C/0AvrII (SEQ ID NO: 5). The amplified product was cloned into the SmaI site of pBstKS+(Stratagene Cloning Systems) to form pBGC218.

pBGC219 was formed by cloning the 0.15 kb AccI-NsiI fragment of pBGC218 into pBGC235. A 0.05 kb synthetic AvrII fragment was formed by annealing PYCS.1p (SEQ ID NO: 8) with PYCS.1m (SEQ ID NO: 9) and the resulting double stranded fragment, encoding the leaky-stop signal and the *P. yoelii* B-cell malarial epitope, was cloned into the AvrII site of pBGC219 to form pBGC221. The 1.0 kb NcoI-KpnI fragment of pBGC221 was cloned into pBGC152 to form pBGC261.

The virus TMV261, produced by transcription of plasmid pBGC261 in vitro, contains a leaky stop signal at the C terminus of the coat protein gene and is therefore predicted to synthesize wild type and recombinant coat proteins at a ratio of 20:1. The recombinant TMVCP fusion synthesized by TMV261 is listed in (SEQ ID NO: 19) with the stop codon decoded as the amino acid Y (amino acid residue 160). The wild type sequence, synthesized by the same virus, is listed in (SEQ ID NO: 21). The epitope (QGPGAP)2 is calculated to be present at 0.3% of the weight of the virion.

Propagation and purification of the epitope expression vector. Infectious transcripts were synthesized from KpnI-linearized pBGC261 using SP6 RNA polymerase and cap (7mGpppG) according to the manufacturer (Gibco/BRL Life Technologies).

An increased quantity of recombinant virus was obtained by passaging and purifying Sample ID No. TMV261.B1b as described in example 1. Six tobacco plants were grown for 27 days post inoculation, accumulating 205 g fresh weight of harvested leaf biomass not including the two lower inoculated leaves. Purified Sample ID No. TMV261.1B2 was recovered (252 mg) at a yield of 1.2 mg virion per gram of fresh weight. Therefore, 4 µg of 12-mer peptide was obtained per gram of fresh weight extracted. Tobacco plants infected with TMV261 accumulated greater than 3.9 micromoles of peptide per kilogram of leaf tissue.

Figure 5:
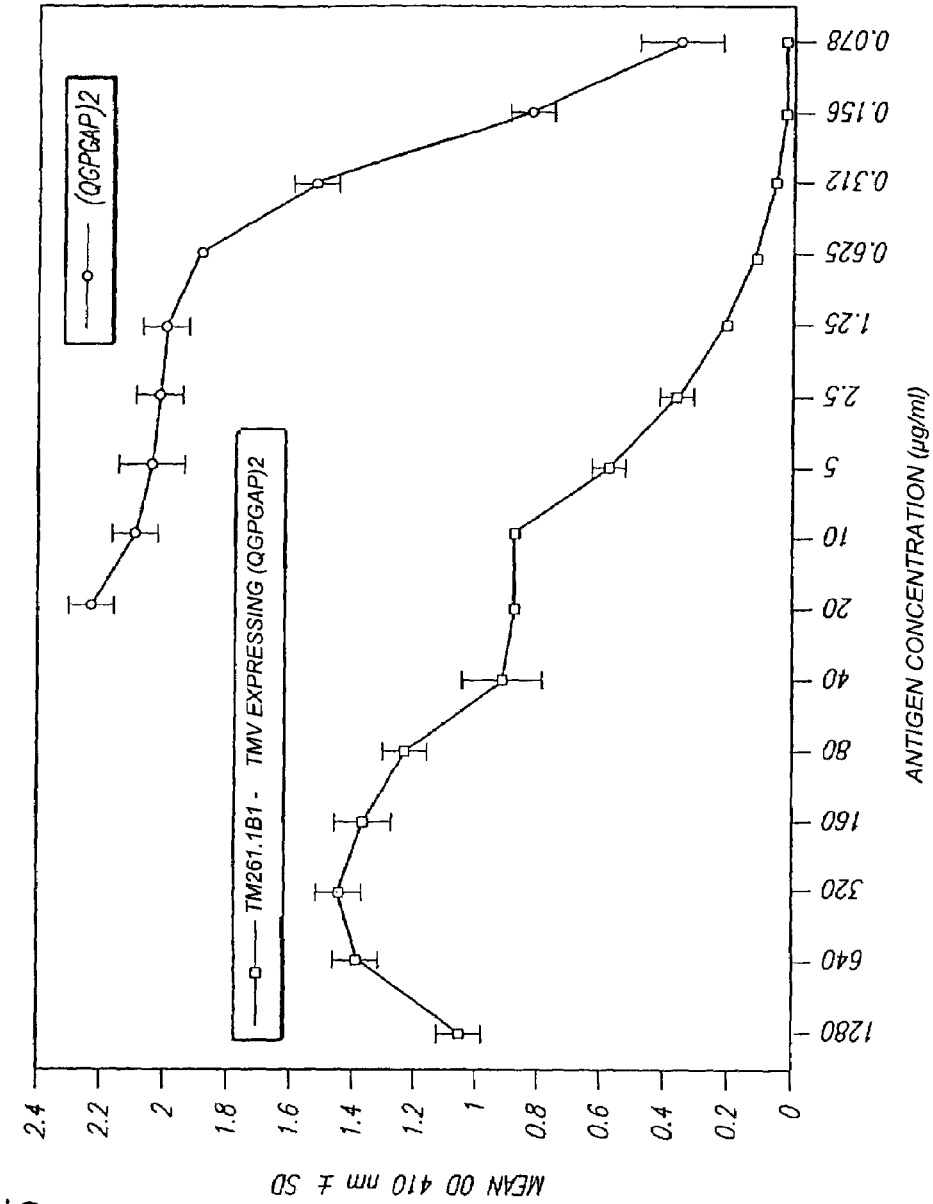
FIG. 5. Monoclonal Antibody (NYS1) Binding to TMV261
The reactivity of NYS1 to the malaria epitope present in TMV261 is measured in a standard ELISA.

Product analysis. The content of the epitope QGPGAP in the virus TMV261 was determined by ELISA with monoclonal antibody NYS1 (FIG. 5). From the titration curve, 50 ug/ml of TMV261 gave the same O. D. reading (1.0) as 0.2 ug/ml of (QGPGAP)2. The measured value of approximately 0.4% of the weight of the virion as epitope is in good agreement with the calculated value of 0.3%. By Western blot analysis, NYS1 cross-reacted only with the TMV261 cp fusion at 19 kD and did not cross-react with the wild type cp or cp fusion present in TMV291. The genomic sequence of the epitope coding region was confirmed by directly sequencing viral RNA extracted from Sample ID. No. TMV261.1B2.

Example 4

Production of a malarial CTL epitope genetically fused to the C terminus of the TMVCP Malarial immunity induced in mice by irradiated sporozoites of P. yoelii is also dependent on CD8+ T lymphocytes. Clone B is one cytotoxic T lymphocyte (CTL) cell clone shown to recognize an epitope present in both the P. yoelii and P. berghei CS proteins. Clone B recognizes the following amino acid sequence; SYVPSAEQILEFVKQISSQ (SEQ ID NO: 23) and when adoptively transferred to mice protects against infection from both species of malaria sporozoites (Weiss et al., 1992). Construction of a genetically modified tobamovirus designed to carry this malarial CTL epitope fused to the surface of virus particles is set forth herein.

Construction of plasmid pBGC289. A 0.5 kb fragment of pBGC11 was PCR amplified using the 5' primer TB2ClaI5' (SEQ ID NO: 3) and the 3' primer C/-5AvrII (SEQ ID NO: 10). The amplified product was cloned into the SmaI site of pBstKS+(Stratagene Cloning Systems) to form pBGC214.

pBGC215 was formed by cloning the 0.15 kb AccI-NsiI fragment of pBGC214 into pBGC235. The 0.9 kb NcoI-KpnI fragment from pBGC215 was cloned into pBGC152 to form pBGC216.

A 0.07 kb synthetic fragment was formed by annealing PYCS.2p (SEQ ID NO: 11) with PYCS.2m (SEQ ID NO: 12) and the resulting double stranded fragment, encoding the P. yoelii CTL malarial epitope, was cloned into the AvrII site of pBGC215 made blunt ended by treatment with mung bean nuclease and creating a unique AatII site, to form pBGC262. A 0.03 kb synthetic AatII fragment was formed by annealing TLS.1EXP (SEQ ID NO: 13) with TLS.1EXM (SEQ ID NO: 14) and the resulting double stranded fragment, encoding the leaky-stop sequence and a stuffer sequence used to facilitate cloning, was cloned into AatII digested pBGC262 to form pBGC263. pBGC262 was digested with AatII and ligated to itself removing the 0.02 kb stuffer fragment to form pBGC264. The 1.0 kb NcoI-KpnI fragment of pBGC264 was cloned into pSNC004 to form pBGC289.

The virus TMV289 produced by transcription of plasmid pBGC289 in vitro, contains a leaky stop signal resulting in the removal of four amino acids from the C terminus of the wild type TMV coat protein gene and is therefore predicted to synthesize a truncated coat protein and a coat protein with a CTL epitope fused at the C terminus at a ratio of 20:1. The recombinant TMVCP/CTL epitope fusion present in TMV289 is listed in SEQ ID NO: 25 with the stop codon decoded as the amino acid Y (amino acid residue 156). The wild type sequence minus four amino acids from the C terminus is listed in SEQ ID NO: 26. The amino acid sequence of the coat protein of virus TMV216 produced by transcription of the plasmid pBGC216 in vitro, is also truncated by four amino acids. The epitope SYVPSAEQILEFVKQISSQ (SEQ ID NO: 23) is calculated to be present at approximately 0.5% of the weight of the virion using the same assumptions confirmed by quantitative ELISA analysis of the readthrough properties of TMV261 in example 3.

Propagation and purification of the epitope expression vector. Infectious transcripts were synthesized from KpnI-linearized pBGC289 using T7 RNA polymerase and cap (7mGpppG) according to the manufacturer (New England Biolabs).

An increased quantity of recombinant virus was obtained by passaging Sample ID No. TMV289.11B1a as described in example 1. Fifteen tobacco plants were grown for 33 days post inoculation accumulating 595 g fresh weight of harvested leaf biomass not including the two lower inoculated leaves. Purified Sample ID. No. TMV289.11B2 was recovered (383 mg) at a yield of 0.6 mg virion per gram of fresh weight. Therefore, 3 μg of 19-mer peptide was obtained per gram of fresh weight extracted. Tobacco plants infected with TMV289 accumulated greater than 1.4 micromoles of peptide per kilogram of leaf tissue.

Product analysis. Partial confirmation of the sequence of the epitope coding region of TMV289 was obtained by restriction digestion analysis of PCR amplified cDNA using viral RNA isolated from Sample ID. No. TMV289.11B2. The presence of proteins in TMV289 with the predicted mobility of the cp fusion at 20 kD and the truncated cp at 17.1 kD was confirmed by denaturing polyacrylamide gel electrophoresis.

Literature Cited

Ahlquist, P. G., and French, R. C. 1986. RNA transformation vector. European Patent Appl. 194,809.

Bruening, G., 1978. Comovirus group, C.M.I./A.A.B. Descriptions of plant viruses, No. 199. Wm. Culross and Son Ltd., Coupar Angus, Perthshire, Scotland.

Butler, P. J. G., Mayo, M. A. 1987. Molecular architecture and assembly of tobacco mosaic virus particles, The molecular biology of the positive strand RNA viruses. (D. J. Rowlands, M. A. Mayo, and B. W. J. Mahy, eds.), Academic Press, London. pp. 237–257.

Charoenvit, Y., Collins, W. E., Jones, T. R., Millet, P., Yuan, L., Beaudoin, R. L., Broderson, J. R., and Hoffman, S. L. 1991a. Inability of malaria vaccine to induce antibodies to a protective epitope within its sequence. Science 251: 668–671.

Charoenvit, Y., Mellouk, S., Cole, C., Bechara, R., Leef, M. F., Sedegah, M., Yuan, L., Robey, F. A., Beaudoin, R. L., and Hoffman, S. L. 1991b. Monoclonal, but not polyclonal, antibodies protect against Plasmodium yoelii sporozoites. J. Immunol. 146:1020–1025.

Dawson, W. O., Beck, D. L., Knorr, D. A., and Grantham, G. L. 1986. cDNA cloning of the complete genome of tobacco mosaic virus and production of infectious transcripts. Proc. Natl. Acad. Sci. USA 83:1832–1836.

Dawson, W. O., Bubrick, P., and Grantham, G. L. 1988. Modifications of the tobacco mosaic virus coat protein gene affecting replication, movement, and symptomatology. Phytopathology 78:783–789.

Dawson, W. O., Lewandowski, D. J., Hilf, M. E., Bubrick, P., Raffo, A. J., Shaw, J. J., Grantham, G. L., and Desjardins, P. R. 1989. A tobacco mosaic virus-hybrid expresses and loses an added gene. Virology 172:285–292.

Donson, J., Kearney, C. M., Hilf, M. E., and Dawson, W. O. 1991. Systemic expression of a bacterial gene by a tobacco mosaic virus-based vector. Proc. Natl. Acad. Sci. USA 88:7204–7208.

Donson, J., Dawson, W. O., Grantham, G. L., Turpen, T. H., Turpen, A. M., Garger, S. J., and Grill, L. K. 1992. Recombinant viral vectors having heterologous subgenomic promoters for systemic expression of foreign genes. U.S. patent application Ser. No. 923,692.

French, R., Janda, M., and Ahlquist, P. 1986. Bacterial gene inserted in an engineered RNA virus: Efficient expression in monocotyledonous plant cells. Science 231:1294–1297.

Gibbs, A. J. 1977. Tobamovirus group, C.M.I./A.A.B. Descriptions of plant viruses, No. 184. Wm. Culross and Son Ltd., Coupar Angus, Perthshire, Scotland.

Goelet, P., Lomonossoff, G. P., Butler P. J. G., Akam, M. E., and Karn, J. 1982. Nucleotide sequence of tobacco mosaic virus RNA. Proc. Natl. Acad. Sci. USA 79:5818–5822.

Gooding, Jr., G. V., and Hebert, T. T. 1967. A simple technique for purification of tobacco mosaic virus in large quantities. Phytopathology 57:1285.

Hamamoto, H., Hashida, E., Matsunaga, Y., Nakagawa, N., Nakanishi, N., Okada, Y., Sugiyama, Y., and Tsuchimoto, S. 1993a. Plant virus vector for foreign gene expression—contains foreign gene down stream of viral coat protein gene, linked by read-through sequence. PCT Patent Application Wo 93/JP408.

Hamamoto, H., Sugiyama, Y., Nakagawa, N., Hashida, E., Matsunaga, Y., Takemoto, S., Watanabe Y., and Okada, Y. 1993b. A new tobacco mosaic virus vector and its use for the systemic production of angiotensin-I-converting enzyme inhibitor in transgenic tobacco and tomato. Bio/Technology 11:930–932.

Haynes, J. R., Cunningham, J., von Seefried, A., Lennick, M., Garvin, R. T., and Shen, S.-H. 1986. Development of a genetically-engineered, candidate polio vaccine employing the self-assembling properties of the tobacco mosaic virus coat protein. Bio/Technology 4:637–641.

James, E. A., Garvin, R. T., and Haynes, J. R. 1985.
Multispecific immunogenic proteins. European Patent Application, 174,759.

Krebbers, E., Bosch, D., and Vandekerckhove, J. 1992.
Prospects and progress in the production of foreign proteins and peptides in plants, Plant Protein Engineering. (P. R. Shewry and S. Gutteridge, eds.), Cambridge University Press, Cambridge. pp. 316–324.

Kumagai, M. H., Turpen, T. H., Weinzettl, N., della-Cioppa, G., Turpen, A. M., Donson, J., Hilf, M. E., Grantham, G. L., Dawson, W. O., Chow, T. P., Piatak Jr., M., and Grill, L. K. 1993. Rapid, high level expression of biologically active α-trichosanthin in transfected plants by a novel RNA viral vector. Proc. Natl. Acad. Sci. USA 90:427–430.

Lomonossoff, G. P., and Johnson, J. E. 1992. Modified plant viruses as vectors. PCT Application WO 92/18618.

Mason, H. S., Lam, D. M-K., and Arntzen, C. J. 1992. Expression of hepatitis B surface antigen in transgenic plants. Proc. Natl. Acad. Sci. USA 89:11745–11749.

Okada, Y., and Han, K. 1986. Plant virus RNA vector. Japanese Patent Application 61/158443.

Okada, Y., and Takamatsu, N. 1988. A plant virus RNA vector. Japanese Patent Application 63/200789.

Pelcher, L. E., Halasa, M. C. 1982. An RNA plant virus vector or portion thereof, a method of construction thereof, and a method of producing a gene derived product therefrom. European Patent Appl. 067,553.

Pelham, H. R. B. 1978. Leaky UAG termination codon in tobacco mosaic virus RNA. Nature 272:469–471.

Skuzeski, J. M., Nichols, L. M., Gesteland, R. F., and Atkins, J. F. 1991. The signal for a leaky UAG stop codon in several plant viruses includes the two downstream codons. J. Mol. Biol. 218:365–373

Takamatsu, N., Ishikawa, M., Meshi, T., and Okada, Y. 1987. Expression of bacterial chloramphenicol acetyltransferase gene in tobacco plants mediated by TMV-RNA. EMBO J. 6:307–311.

Takamatsu, N., Watanabe, Y., Yanagi, H., Meshi, T., Shiba, T., and Okada, Y. 1990. Production of enkephalin in tobacco protoplasts using tobacco mosaic virus RNA vector. FEBS Lett. 269:73–76.

Turpen, T. H., and Grill, L. K. Apr. 4, 1989. New products through viral coat protein modification. Biosource Genetics Corporation, Record of Invention, First Written Disclosure.

Usha, R., Rohll, J. B., Spall, V. E., Shanks, M., Maule, A. J., Johnson, J. E., and Lomonossoff, G. P. 1993. Expression of an animal virus antigenic site on the surface of a plant virus particle. Virology 197:366–374.

van Kammen, A., and de Jager, C. P. 1978. Cowpea mosaic virus, C.M.I./A.A.B. Descriptions of plant viruses, No. 197. Wm. Culross and Son Ltd., Coupar Angus, Perthshire, Scotland.

Weiss, W. R., Berzofsky, J. A., Houghten, R. A., Sedegah, M., Hollindale, M., and Hoffman, S. L. 1992. A T cell clone directed at the circumsporozoite protein which protects mice against both *Plasmodium yoelii* and *Plasmodium berghei*. J. Immunol. 149:2103–2109.

Zaitlin, M., and Israel, H. W. 1975. Tobacco mosaic virus (type strain), C.M.I./A.A.B. Descriptions of plant viruses, No. 151. Wm. Culross and Son Ltd., Coupar Angus, Perthshire, Scotland.

Incorporation by Reference

All patents, patents applications, and publications cited are incorporated herein by reference.

Equivalents

The foregoing written specification is considered to be sufficient to enable one skilled in the art to practice the invention. Indeed, various modifications of the above-described makes for carrying out the invention which are obvious to those skilled in the field of molecular biology or related fields are intended to be within the scope of the following claims.

What is claimed is:

1. A virion particle comprising a coat protein of a Tobamovirus and a fusion protein of the coat protein and a foreign protein.

2. A process for systemically expressing a fusion protein of a coat protein of a Tobamovirus and a foreign protein in a plant comprising the steps of:

(a) inoculating a plant with a plant virus vector, such that upon expression of the vector in a plant, the coat protein of a Tobamovirus and the fusion protein of the coat protein and the foreign protein are systemically produced in the plant; and (b) expressing the fusion protein systemically in the plant.

* * * * *

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
       (A) LENGTH: 49 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO: 1:

GGAATTCAAG CTTAATACGA CTCACTATAG TATTTTTACA ACAATTACC          49

(2) INFORMATION FOR SEQ ID NO: 2:

(i) SEQUENCE CHARACTERISTICS:
       (A) LENGTH: 18 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO: 2:

CCTTCATGTA AACCTCTC          18

(2) INFORMATION FOR SEQ ID NO: 3:

(i) SEQUENCE CHARACTERISTICS:
       (A) LENGTH: 25 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO: 3:

TAATCGATGA TGATTCGGAG GCTAC          25

(2) INFORMATION FOR SEQ ID NO: 4:

(i) SEQUENCE CHARACTERISTICS:
       (A) LENGTH: 36 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO: 4:

AAAGTCTCTG TCTCCTGCAG GGAACCTAAC AGTTAC          36

(2) INFORMATION FOR SEQ ID NO: 5:

(i) SEQUENCE CHARACTERISTICS:
       (A) LENGTH: 36 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO: 5:

ATTATGCATC TTGACTACCT AGGTTGCAGG ACCAGA                    36

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 6:

GGCGATCGGG CTGGTGACCG TGCA                                 24

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 7:

CGGTCACCAG CCCGATCGCC TGCA                                 24

(2) INFORMATION FOR SEQ ID NO: 8:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 8:

CTAGCAATTA CAAGGTCCAG GTGCACCTCA AGGTCCTGGA GCTCC           45

(2) INFORMATION FOR SEQ ID NO: 9:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 9:

CTAGGGAGCT CCAGGACCTT GAGGTGCACC TGGACCTTGT AATTG           45

(2) INFORMATION FOR SEQ ID NO: 10:

(i) SEQUENCE CHARACTERISTICS:
        (A) LENGTH: 35 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 10:

ATTATGCATC TTGACTACCT AGGTCCAAAC CAAAC                      35

(2) INFORMATION FOR SEQ ID NO: 11:

(i) SEQUENCE CHARACTERISTICS:
        (A) LENGTH: 66 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 11:

```
GTCATATGTT CCATCTGCAG AGCAGATCTT GGAATTCGTT AAGCAAATCT CGAGTCAGTA      60

ACTATA                                                                 66
```

(2) INFORMATION FOR SEQ ID NO: 12:

(i) SEQUENCE CHARACTERISTICS:
        (A) LENGTH: 66 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 12:

```
TATAGTTACT GACTCGAGAT TTGCTTAACG AATTCCAAGA TCTGCTCTGC AGATGGAACA      60

TATGAC                                                                 66
```

(2) INFORMATION FOR SEQ ID NO: 13:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 13:

```
CGACCTAGGT GATGACGTCA TAGCAATTAA CGT                                   33
```

(2) INFORMATION FOR SEQ ID NO: 14:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 14:

```
TAATTGCTAT GACGTCATCA CCTAGGTCGA CGT                                   33
```

(2) INFORMATION FOR SEQ ID NO: 15:

(i) SEQUENCE CHARACTERISTICS:
        (A) LENGTH: 4 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO: 15:

```
Ala Gly Asp Arg
 1
```

(2) INFORMATION FOR SEQ ID NO: 16:

(i) SEQUENCE CHARACTERISTICS:
        (A) LENGTH: 510 base pairs
        (B) TYPE: nucleic acid
        (C) STRANDEDNESS: unknown
        (D) TOPOLOGY: unknown (ii) MOLECULE TYPE: DNA (genomic)

(vi) ORIGINAL SOURCE:
        (A) ORGANISM: pBGC291 Fusion (ix) FEATURE:
        (A) NAME/KEY: CDS
        (B) LOCATION: 1..510

(xi) SEQUENCE DESCRIPTION: SEQ ID NO: 16:

```
ATG TCT TAC AGT ATC ACT ACT CCA TCT CAG TTC GTG TTC TTG TCA TCA      48
Met Ser Tyr Ser Ile Thr Thr Pro Ser Gln Phe Val Phe Leu Ser Ser
 1               5                  10                  15

GCG TGG GCC GAC CCA ATA GAG TTA ATT AAT TTA TGT ACT AAT GCC TTA      96
Ala Trp Ala Asp Pro Ile Glu Leu Ile Asn Leu Cys Thr Asn Ala Leu
             20                  25                  30

GGA AAT CAG TTT CAA ACA CAA CAA GCT CGA ACT GTC GTT CAA AGA CAA     144
Gly Asn Gln Phe Gln Thr Gln Gln Ala Arg Thr Val Val Gln Arg Gln
         35                  40                  45

TTC AGT GAG GTG TGG AAA CCT TCA CCA CAA GTA ACT GTT AGG TTC CCT     192
Phe Ser Glu Val Trp Lys Pro Ser Pro Gln Val Thr Val Arg Phe Pro
 50                  55                  60

GCA GGC GAT CGG GCT GGT GAC CGT GCA GGA GAC AGA GAC TTT AAG GTG     240
Ala Gly Asp Arg Ala Gly Asp Arg Ala Gly Asp Arg Asp Phe Lys Val
 65                  70                  75                  80

TAC AGG TAC AAT GCG GTA TTA GAC CCG CTA GTC ACA GCA CTG TTA GGT     288
Tyr Arg Tyr Asn Ala Val Leu Asp Pro Leu Val Thr Ala Leu Leu Gly
                 85                  90                  95

GCA TTC GAC ACT AGA AAT AGA ATA ATA GAA GTT GAA AAT CAG GCG AAC     336
Ala Phe Asp Thr Arg Asn Arg Ile Ile Glu Val Glu Asn Gln Ala Asn
             100                 105                 110

CCC ACG ACT GCC GAA ACG TTA GAT GCT ACT CGT AGA GTA GAC GAC GCA     384
Pro Thr Thr Ala Glu Thr Leu Asp Ala Thr Arg Arg Val Asp Asp Ala
         115                 120                 125

ACG GTG GCC ATA AGG AGC GCG ATA AAT AAT TTA ATA GTA GAA TTG ATC     432
Thr Val Ala Ile Arg Ser Ala Ile Asn Asn Leu Ile Val Glu Leu Ile
 130                 135                 140

AGA GGA ACC GGA TCT TAT AAT CGG AGC TCT TTC GAG AGC TCT TCT GGT     480
Arg Gly Thr Gly Ser Tyr Asn Arg Ser Ser Phe Glu Ser Ser Ser Gly
145                 150                 155                 160

TTG GTT TGG ACC TCT GGT CCT GCA ACT TGA                             510
Leu Val Trp Thr Ser Gly Pro Ala Thr
                165
```

(2) INFORMATION FOR SEQ ID NO: 17:

(i) SEQUENCE CHARACTERISTICS:
        (A) LENGTH: 169 amino acids
        (B) TYPE: amino acid
        (D) TOPOLOGY: linear (ii) MOLECULE TYPE: protein (vi) ORIGINAL SOURCE:
        (A) ORGANISM: pBGC291 Fusion (xi) SEQUENCE DESCRIPTION: SEQ ID NO: 17:

```
Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Ala Arg Thr Val Gln Arg Gln
        35                  40                  45

Phe Ser Glu Val Trp Lys Pro Ser Pro Gln Val Thr Val Arg Phe Pro
    50                  55                  60

Ala Gly Asp Arg Ala Gly Asp Arg Ala Gly Asp Arg Asp Phe Lys Val
65                  70                  75                  80

Tyr Arg Tyr Asn Ala Val Leu Asp Pro Leu Val Thr Ala Leu Leu Gly
                85                  90                  95

Ala Phe Asp Thr Arg Asn Arg Ile Ile Glu Val Glu Asn Gln Ala Asn
                100                 105                 110

Pro Thr Thr Ala Glu Thr Leu Asp Ala Thr Arg Arg Val Asp Asp Ala
                115                 120                 125

Thr Val Ala Ile Arg Ser Ala Ile Asn Asn Leu Ile Val Glu Leu Ile
130                 135                 140

Arg Gly Thr Gly Ser Tyr Asn Arg Ser Ser Phe Glu Ser Ser Gly
145                 150                 155                 160

Leu Val Trp Thr Ser Gly Pro Ala Thr
                165
```

(2) INFORMATION FOR SEQ ID NO: 18:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO: 18:

```
Gln Gly Pro Gly Ala Pro
1               5
```

(2) INFORMATION FOR SEQ ID NO: 19:

(i) SEQUENCE CHARACTERISTICS:
        (A) LENGTH: 525 base pairs
        (B) TYPE: nucleic acid
        (C) STRANDEDNESS: unknown
        (D) TOPOLOGY: unknown (ii) MOLECULE TYPE: DNA (genomic)

(vi) ORIGINAL SOURCE:
        (A) ORGANISM: pBGC261 Leaky Stop (ix) FEATURE:
        (A) NAME/KEY: CDS
        (B) LOCATION: 1..525

(xi) SEQUENCE DESCRIPTION: SEQ ID NO: 19:

```
ATG TCT TAC AGT ATC ACT ACT CCA TCT CAG TTC GTG TTC TTG TCA TCA    48
Met Ser Tyr Ser Ile Thr Thr Pro Ser Gln Phe Val Phe Leu Ser Ser
1               5                   10                  15

GCG TGG GCC GAC CCA ATA GAG TTA ATT AAT TTA TGT ACT AAT GCC TTA    96
Ala Trp Ala Asp Pro Ile Glu Leu Ile Asn Leu Cys Thr Asn Ala Leu
            20                  25                  30
```

-continued

```
GGA AAT CAG TTT CAA ACA CAA CAA GCT CGA ACT GTC GTT CAA AGA CAA        144
Gly Asn Gln Phe Gln Thr Gln Gln Ala Arg Thr Val Val Gln Arg Gln
         35                  40                  45

TTC AGT GAG GTG TGG AAA CCT TCA CCA CAA GTA ACT GTT AGG TTC CCT        192
Phe Ser Glu Val Trp Lys Pro Ser Pro Gln Val Thr Val Arg Phe Pro
 50                  55                  60

GAC AGT GAC TTT AAG GTG TAC AGG TAC AAT GCG GTA TTA GAC CCG CTA        240
Asp Ser Asp Phe Lys Val Tyr Arg Tyr Asn Ala Val Leu Asp Pro Leu
 65                  70                  75                  80

GTC ACA GCA CTG TTA GGT GCA TTC GAC ACT AGA AAT AGA ATA ATA GAA        288
Val Thr Ala Leu Leu Gly Ala Phe Asp Thr Arg Asn Arg Ile Ile Glu
             85                  90                  95

GTT GAA AAT CAG GCG AAC CCC ACG ACT GCC GAA ACG TTA GAT GCT ACT        336
Val Glu Asn Gln Ala Asn Pro Thr Thr Ala Glu Thr Leu Asp Ala Thr
                100                 105                 110

CGT AGA GTA GAC GAC GCA ACG GTG GCC ATA AGG AGC GCG ATA AAT AAT        384
Arg Arg Val Asp Asp Ala Thr Val Ala Ile Arg Ser Ala Ile Asn Asn
            115                 120                 125

TTA ATA GTA GAA TTG ATC AGA GGA ACC GGA TCT TAT AAT CGG AGC TCT        432
Leu Ile Val Glu Leu Ile Arg Gly Thr Gly Ser Tyr Asn Arg Ser Ser
130                 135                 140

TTC GAG AGC TCT TCT GGT TTG GTT TGG ACC TCT GGT CCT GCA ACC TAG        480
Phe Glu Ser Ser Ser Gly Leu Val Trp Thr Ser Gly Pro Ala Thr Tyr
145                 150                 155                 160

CAA TTA CAA GGT CCA GGT GCA CCT CAA GGT CCT GGA GCT CCC TAG            525
Gln Leu Gln Gly Pro Gly Ala Pro Gln Gly Pro Gly Ala Pro
                165                 170                 175
```

(2) INFORMATION FOR SEQ ID NO: 20:

(i) SEQUENCE CHARACTERISTICS:
        (A) LENGTH: 174 amino acids
        (B) TYPE: amino acid
        (D) TOPOLOGY: linear (ii) MOLECULE TYPE: protein (vi) ORIGINAL SOURCE:
        (A) ORGANISM: pBGC261 Leaky Stop (xi) SEQUENCE DESCRIPTION: SEQ ID NO: 20:

```
Met Ser Tyr Ser Ile Thr Thr Pro Ser Gln Phe Val Phe Leu Ser Ser
 1               5                  10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
         35                  40                  45

Phe Ser Glu Val Trp Lys Pro Ser Pro Gln Val Thr Val Arg Phe Pro
 50                  55                  60

Asp Ser Asp Phe Lys Val Tyr Arg Tyr Asn Ala Val Leu Asp Pro Leu
 65                  70                  75                  80

Val Thr Ala Leu Leu Gly Ala Phe Asp Thr Arg Asn Arg Ile Ile Glu
             85                  90                  95

Val Glu Asn Gln Ala Asn Pro Thr Thr Ala Glu Thr Leu Asp Ala Thr
                100                 105                 110

Arg Arg Val Asp Asp Ala Thr Val Ala Ile Arg Ser Ala Ile Asn Asn
            115                 120                 125

Leu Ile Val Glu Leu Ile Arg Gly Thr Gly Ser Tyr Asn Arg Ser Ser
130                 135                 140
```

-continued

```
Phe Glu Ser Ser Ser Gly Leu Val Trp Thr Ser Gly Pro Ala Thr Tyr
145                 150                 155                 160

Gln Leu Gln Gly Pro Gly Ala Pro Gln Gly Pro Gly Ala Pro
                165                 170
```

(2) INFORMATION FOR SEQ ID NO: 21:

(i) SEQUENCE CHARACTERISTICS:
        (A) LENGTH: 480 base pairs
        (B) TYPE: nucleic acid
        (C) STRANDEDNESS: unknown
        (D) TOPOLOGY: unknown (ii) MOLECULE TYPE: DNA (genomic)

(vi) ORIGINAL SOURCE:
        (A) ORGANISM: pBGC261 Nonfusion (ix) FEATURE:
        (A) NAME/KEY: CDS
        (B) LOCATION: 1..480

(xi) SEQUENCE DESCRIPTION: SEQ ID NO: 21:

```
ATG TCT TAC AGT ATC ACT ACT CCA TCT CAG TTC GTG TTC TTG TCA TCA      48
Met Ser Tyr Ser Ile Thr Thr Pro Ser Gln Phe Val Phe Leu Ser Ser
1               5                   10                  15

GCG TGG GCC GAC CCA ATA GAG TTA ATT AAT TTA TGT ACT AAT GCC TTA      96
Ala Trp Ala Asp Pro Ile Glu Leu Ile Asn Leu Cys Thr Asn Ala Leu
                20                  25                  30

GGA AAT CAG TTT CAA ACA CAA CAA GCT CGA ACT GTC GTT CAA AGA CAA     144
Gly Asn Gln Phe Gln Thr Gln Gln Ala Arg Thr Val Val Gln Arg Gln
            35                  40                  45

TTC AGT GAG GTG TGG AAA CCT TCA CCA CAA GTA ACT GTT AGG TTC CCT     192
Phe Ser Glu Val Trp Lys Pro Ser Pro Gln Val Thr Val Arg Phe Pro
50                  55                  60

GAC AGT GAC TTT AAG GTG TAC AGG TAC AAT GCG GTA TTA GAC CCG CTA     240
Asp Ser Asp Phe Lys Val Tyr Arg Tyr Asn Ala Val Leu Asp Pro Leu
65                  70                  75                  80

GTC ACA GCA CTG TTA GGT GCA TTC GAC ACT AGA AAT AGA ATA ATA GAA     288
Val Thr Ala Leu Leu Gly Ala Phe Asp Thr Arg Asn Arg Ile Ile Glu
                85                  90                  95

GTT GAA AAT CAG GCG AAC CCC ACG ACT GCC GAA ACG TTA GAT GCT ACT     336
Val Glu Asn Gln Ala Asn Pro Thr Thr Ala Glu Thr Leu Asp Ala Thr
            100                 105                 110

CGT AGA GTA GAC GAC GCA ACG GTG GCC ATA AGG AGC GCG ATA AAT AAT     384
Arg Arg Val Asp Asp Ala Thr Val Ala Ile Arg Ser Ala Ile Asn Asn
        115                 120                 125

TTA ATA GTA GAA TTG ATC AGA GGA ACC GGA TCT TAT AAT CGG AGC TCT     432
Leu Ile Val Glu Leu Ile Arg Gly Thr Gly Ser Tyr Asn Arg Ser Ser
130                 135                 140

TTC GAG AGC TCT TCT GGT TTG GTT TGG ACC TCT GGT CCT GCA ACC TAG     480
Phe Glu Ser Ser Ser Gly Leu Val Trp Thr Ser Gly Pro Ala Thr
145                 150                 155                 160
```

(2) INFORMATION FOR SEQ ID NO: 22:

(i) SEQUENCE CHARACTERISTICS:
        (A) LENGTH: 159 amino acids
        (B) TYPE: amino acid
        (D) TOPOLOGY: linear (ii) MOLECULE TYPE: protein (vi) ORIGINAL SOURCE:
        (A) ORGANISM: pBGC261 Nonfusion (xi) SEQUENCE DESCRIPTION: SEQ ID NO: 22:

```
Met Ser Tyr Ser Ile Thr Thr Pro Ser Gln Phe Val Phe Leu Ser Ser
 1               5                  10                  15

Ala Trp Ala Asp Pro Ile Glu Leu Ile Asn Leu Cys Thr Asn Ala Leu
             20                  25                  30

Gly Asn Gln Phe Gln Thr Gln Ala Arg Thr Val Gln Arg Gln
             35                  40                  45

Phe Ser Glu Val Trp Lys Pro Ser Pro Gln Val Thr Val Arg Phe Pro
 50                  55                  60

Asp Ser Asp Phe Lys Val Tyr Arg Tyr Asn Ala Val Leu Asp Pro Leu
 65                  70                  75                  80

Val Thr Ala Leu Leu Gly Ala Phe Asp Thr Arg Asn Arg Ile Ile Glu
             85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
            115                 120                 125

Leu Ile Val Glu Leu Ile Arg Gly Thr Gly Ser Tyr Asn Arg Ser Ser
130                 135                 140

Phe Glu Ser Ser Ser Gly Leu Val Trp Thr Ser Gly Pro Ala Thr
145                 150                 155
```

(2) INFORMATION FOR SEQ ID NO: 23:

(i) SEQUENCE CHARACTERISTICS:
        (A) LENGTH: 19 amino acids
        (B) TYPE: amino acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 23:

```
Ser Tyr Val Pro Ser Ala Glu Gln Ile Leu Glu Phe Val Lys Gln Ile
 1               5                  10                  15

Ser Ser Gln
```

(2) INFORMATION FOR SEQ ID NO: 24:

(i) SEQUENCE CHARACTERISTICS:
        (A) LENGTH: 537 base pairs
        (B) TYPE: nucleic acid
        (C) STRANDEDNESS: unknown
        (D) TOPOLOGY: unknown (ii) MOLECULE TYPE: DNA (genomic)

(vi) ORIGINAL SOURCE:
        (A) ORGANISM: pBGC289 Leaky Stop (ix) FEATURE:
        (A) NAME/KEY: CDS
        (B) LOCATION: 1..537

(xi) SEQUENCE DESCRIPTION: SEQ ID NO: 24:

```
ATG TCT TAC AGT ATC ACT ACT CCA TCT CAG TTC GTG TTC TTG TCA TCA    48
Met Ser Tyr Ser Ile Thr Thr Pro Ser Gln Phe Val Phe Leu Ser Ser
 1               5                  10                  15

GCG TGG GCC GAC CCA ATA GAG TTA ATT AAT TTA TGT ACT AAT GCC TTA    96
Ala Trp Ala Asp Pro Ile Glu Leu Ile Asn Leu Cys Thr Asn Ala Leu
             20                  25                  30
```

```
GGA AAT CAG TTT CAA ACA CAA CAA GCT CGA ACT GTC GTT CAA AGA CAA       144
Gly Asn Gln Phe Gln Thr Gln Gln Ala Arg Thr Val Val Gln Arg Gln
         35                  40                  45

TTC AGT GAG GTG TGG AAA CCT TCA CCA CAA GTA ACT GTT AGG TTC CCT       192
Phe Ser Glu Val Trp Lys Pro Ser Pro Gln Val Thr Val Arg Phe Pro
 50                  55                  60

GAC AGT GAC TTT AAG GTG TAC AGG TAC AAT GCG GTA TTA GAC CCG CTA       240
Asp Ser Asp Phe Lys Val Tyr Arg Tyr Asn Ala Val Leu Asp Pro Leu
 65                  70                  75                  80

GTC ACA GCA CTG TTA GGT GCA TTC GAC ACT AGA AAT AGA ATA ATA GAA       288
Val Thr Ala Leu Leu Gly Ala Phe Asp Thr Arg Asn Arg Ile Ile Glu
                 85                  90                  95

GTT GAA AAT CAG GCG AAC CCC ACG ACT GCC GAA ACG TTA GAT GCT ACT       336
Val Glu Asn Gln Ala Asn Pro Thr Thr Ala Glu Thr Leu Asp Ala Thr
            100                 105                 110

CGT AGA GTA GAC GAC GCA ACG GTG GCC ATA AGG AGC GCG ATA AAT AAT       384
Arg Arg Val Asp Asp Ala Thr Val Ala Ile Arg Ser Ala Ile Asn Asn
        115                 120                 125

TTA ATA GTA GAA TTG ATC AGA GGA ACC GGA TCT TAT AAT CGG AGC TCT       432
Leu Ile Val Glu Leu Ile Arg Gly Thr Gly Ser Tyr Asn Arg Ser Ser
130                 135                 140

TTC GAG AGC TCT TCT GGT TTG GTT TGG ACG TCA TAG CAA TTA ACG TCA       480
Phe Glu Ser Ser Ser Gly Leu Val Trp Thr Ser Tyr Gln Leu Thr Ser
145                 150                 155                 160

TAT GTT CCA TCT GCA GAG CAG ATC TTG GAA TTC GTT AAG CAA ATC TCG       528
Tyr Val Pro Ser Ala Glu Gln Ile Leu Glu Phe Val Lys Gln Ile Ser
                165                 170                 175

AGT CAG TAG                                                           537
Ser Gln
```

(2) INFORMATION FOR SEQ ID NO: 25:

(i) SEQUENCE CHARACTERISTICS:
        (A) LENGTH: 178 amino acids
        (B) TYPE: amino acid
        (D) TOPOLOGY: linear (ii) MOLECULE TYPE: protein (vi) ORIGINAL SOURCE:
        (A) ORGANISM: pBGC289 Leaky Stop (xi) SEQUENCE DESCRIPTION: SEQ ID NO: 25:

```
Met Ser Tyr Ser Ile Thr Thr Pro Ser Gln Phe Val Phe Leu Ser Ser
 1               5                  10                  15

Ala Trp Ala Asp Pro Ile Glu Leu Ile Asn Leu Cys Thr Asn Ala Leu
             20                  25                  30

Gly Asn Gln Phe Gln Thr Gln Gln Ala Arg Thr Val Val Gln Arg Gln
         35                  40                  45

Phe Ser Glu Val Trp Lys Pro Ser Pro Gln Val Thr Val Arg Phe Pro
 50                  55                  60

Asp Ser Asp Phe Lys Val Tyr Arg Tyr Asn Ala Val Leu Asp Pro Leu
 65                  70                  75                  80

Val Thr Ala Leu Leu Gly Ala Phe Asp Thr Arg Asn Arg Ile Ile Glu
                 85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
        115                 120                 125
```

```
Leu Ile Val Glu Leu Ile Arg Gly Thr Gly Ser Tyr Asn Arg Ser Ser
    130                 135                 140

Phe Glu Ser Ser Ser Gly Leu Val Trp Thr Ser Tyr Gln Leu Thr Ser
145                 150                 155                 160

Tyr Val Pro Ser Ala Glu Gln Ile Leu Glu Phe Val Lys Gln Ile Ser
                165                 170                 175

Ser Gln
```

(2) INFORMATION FOR SEQ ID NO: 26:

(i) SEQUENCE CHARACTERISTICS:
        (A) LENGTH: 468 base pairs
        (B) TYPE: nucleic acid
        (C) STRANDEDNESS: unknown
        (D) TOPOLOGY: unknown (ii) MOLECULE TYPE: DNA (genomic)

(vi) ORIGINAL SOURCE:
        (A) ORGANISM: pBGC289 Non-fusion (ix) FEATURE:
        (A) NAME/KEY: CDS
        (B) LOCATION: 1..468

(xi) SEQUENCE DESCRIPTION: SEQ ID NO: 26:

```
ATG TCT TAC AGT ATC ACT ACT CCA TCT CAG TTC GTG TTC TTG TCA TCA      48
Met Ser Tyr Ser Ile Thr Thr Pro Ser Gln Phe Val Phe Leu Ser Ser
 1               5                  10                  15

GCG TGG GCC GAC CCA ATA GAG TTA ATT AAT TTA TGT ACT AAT GCC TTA      96
Ala Trp Ala Asp Pro Ile Glu Leu Ile Asn Leu Cys Thr Asn Ala Leu
             20                  25                  30

GGA AAT CAG TTT CAA ACA CAA CAA GCT CGA ACT GTC GTT CAA AGA CAA     144
Gly Asn Gln Phe Gln Thr Gln Gln Ala Arg Thr Val Val Gln Arg Gln
         35                  40                  45

TTC AGT GAG GTG TGG AAA CCT TCA CCA CAA GTA ACT GTT AGG TTC CCT     192
Phe Ser Glu Val Trp Lys Pro Ser Pro Gln Val Thr Val Arg Phe Pro
     50                  55                  60

GAC AGT GAC TTT AAG GTG TAC AGG TAC AAT GCG GTA TTA GAC CCG CTA     240
Asp Ser Asp Phe Lys Val Tyr Arg Tyr Asn Ala Val Leu Asp Pro Leu
 65                  70                  75                  80

GTC ACA GCA CTG TTA GGT GCA TTC GAC ACT AGA AAT AGA ATA ATA GAA     288
Val Thr Ala Leu Leu Gly Ala Phe Asp Thr Arg Asn Arg Ile Ile Glu
                 85                  90                  95

GTT GAA AAT CAG GCG AAC CCC ACG ACT GCC GAA ACG TTA GAT GCT ACT     336
Val Glu Asn Gln Ala Asn Pro Thr Thr Ala Glu Thr Leu Asp Ala Thr
            100                 105                 110

CGT AGA GTA GAC GAC GCA ACG GTG GCC ATA AGG AGC GCG ATA AAT AAT     384
Arg Arg Val Asp Asp Ala Thr Val Ala Ile Arg Ser Ala Ile Asn Asn
        115                 120                 125

TTA ATA GTA GAA TTG ATC AGA GGA ACC GGA TCT TAT AAT CGG AGC TCT     432
Leu Ile Val Glu Leu Ile Arg Gly Thr Gly Ser Tyr Asn Arg Ser Ser
    130                 135                 140

TTC GAG AGC TCT TCT GGT TTG GTT TGG ACG TCA TAG                     468
Phe Glu Ser Ser Ser Gly Leu Val Trp Thr Ser
145                 150                 155
```

(2) INFORMATION FOR SEQ ID NO: 27:

(i) SEQUENCE CHARACTERISTICS:
        (A) LENGTH: 155 amino acids
        (B) TYPE: amino acid
        (D) TOPOLOGY: linear -continued

```
    (ii) MOLECULE TYPE: protein (vi) ORIGINAL SOURCE:
         (A) ORGANISM: pBGC289 Non-fusion (xi) SEQUENCE DESCRIPTION: SEQ ID NO: 27:

Met Ser Tyr Ser Ile Thr Thr Pro Ser Gln Phe Val Phe Leu Ser Ser
 1               5                  10                  15

Ala Trp Ala Asp Pro Ile Glu Leu Ile Asn Leu Cys Thr Asn Ala Leu
                20                  25                  30

Gly Asn Gln Phe Gln Thr Gln Gln Ala Arg Thr Val Val Gln Arg Gln
                35                  40                  45

Phe Ser Glu Val Trp Lys Pro Ser Pro Gln Val Thr Val Arg Phe Pro
 50                  55                  60

Asp Ser Asp Phe Lys Val Tyr Arg Tyr Asn Ala Val Leu Asp Pro Leu
 65                  70                  75                  80

Val Thr Ala Leu Leu Gly Ala Phe Asp Thr Arg Asn Arg Ile Ile Glu
                85                  90                  95

Val Glu Asn Gln Ala Asn Pro Thr Thr Ala Glu Thr Leu Asp Ala Thr
                100                 105                 110

Arg Arg Val Asp Asp Ala Thr Val Ala Ile Arg Ser Ala Ile Asn Asn
                115                 120                 125

Leu Ile Val Glu Leu Ile Arg Gly Thr Gly Ser Tyr Asn Arg Ser Ser
                130                 135                 140

Phe Glu Ser Ser Ser Gly Leu Val Trp Thr Ser
145                 150                 155
```